United States Patent [19]

Cates et al.

[11] Patent Number: 6,165,774
[45] Date of Patent: Dec. 26, 2000

[54] PARAINFLUENZA VIRUS GLYCOPROTEINS AND VACCINES

[75] Inventors: George A. Cates, Richmond Hill; Mary E. Ewasyshyn, Willowdale; Raafat E. F. Fahim, Mississauga; Gail E. D. Jackson, Richmond Hill; Michel H. Klein, Willowdale; Alison L. Symington, Toronto, all of Canada

[73] Assignee: Connaught Laboratories Limited, Toronto, Canada

[21] Appl. No.: 09/043,477

[22] PCT Filed: Sep. 23, 1996

[86] PCT No.: PCT/CA96/00639

§ 371 Date: Aug. 7, 1998

§ 102(e) Date: Aug. 7, 1998

[87] PCT Pub. No.: WO97/11093

PCT Pub. Date: Mar. 27, 1997

[51] Int. Cl.$^7$ ..................................................... C12N 7/06
[52] U.S. Cl. ............................................................ 435/238
[58] Field of Search ............................................. 435/238

[56] References Cited

U.S. PATENT DOCUMENTS

4,790,987 12/1988 Compans et al. .
5,256,294 10/1993 Van Reis .

FOREIGN PATENT DOCUMENTS

| 0222415 | 5/1987 | European Pat. Off. . |
| 0522560 | 1/1993 | European Pat. Off. . |
| 2001326 | 1/1979 | United Kingdom . |
| WO88/08718 | 11/1988 | WIPO . |
| WO91/00104 | 1/1991 | WIPO . |
| WO 93/06218 | 4/1993 | WIPO . |

OTHER PUBLICATIONS

Katz, S.L. New vaccine development Establishing Priorities. vol. 1. Washington: National Academic Press. (1985) pp. 385–396.
Murphy, B.R., et al, (1988) Vir. Res. 11, 1–15.
Ray, R., et al, (1993) J. Infect. Dis. 167, 752–755.
Ray, R., et al, (1985) J. Infect. Dis. 152 (6), 1219–1230.
Ray, R., et al (1987) J. Gen. Virol. 68, 409–418.
Ray, R., et al, (1988) J. Infect. Dis. 157 (4), 648–654.
Ray, R., et al, (1990) J. Infect. Dis. 162, 746–749.
Ray, R., (1988) J. Virol. 62 (3), 783–787.
Ewasyshyn, M., et al, (1992) Vaccine 10 (6), 412–420.
Ambrose, M.W., et al, (1991) Vaccine 9, 505–511.
Al–Ahdal, M.N., et al—Biochimica et Biophysica Acta 854 (1986) 157–168.
Asano, et al,—Tokai J. Exp. Clin. Med., vol. 7, Supplement pp. 193–196, (1982).
Gething, M.J., et al—Proc. Natl. Acad. Sci. USA, vol. 75, No. 6, pp. 2737–2740 (1978). Biochemistry.
Hsu–M.C. et al,—Virology 95, 476–491 (1979).
Miura, N., et al Experimental Cell Research 141, (1982) 409–420.
Orvell, C. et al, Journal of Immunology, vol. 119, No. 6, Dec. 1977.
Scalia, G. et al, Clin. Diagnostic Virol. May 1995, vol. 3(4), pp. 351–359.
Sugii, S., FEMS Microbiology Letters 37 (1986) 79–82.
Tsurudome, M., et al Virology 171, 38–48 (1989).
Urata, Dana M., et al Intervirology, 6:108–114 (1975/76).
Welling, G.W., et al—Journal of Chromatography, vol. 266 (1983).
Prehm et al—Chem. Pept, Proteins, Proc. USSR–FRG Symp. $3^{rd}$, 1982, pp. 53–59.
Scheid et al, Virology, vol. 50, No. 3, Dec. 1972, pp. 640–652.
Scheid et al, Virology, vol. 62, No. 1, 1974, pp. 125–133.
Morein, B. et al, Journal of General Virology, vol. 64, No. PART 07, Jul. 1983, pp. 1557–1569.
Fulginiti, V.A., et al, (1969) Am. J. Epidemiol. 89 (4), 435–448.
Chin, J., et al, (1969) Am. J. Epidemiol. 89(4), 449–463.
Jensen, K.E., et al, (1962) J. Immunol. 89, 216–226.
Hall, S.L., et al, (1993) J. Infect. Dis. 167, 958–962.
Belshe, R.B., et al, (1992) J. Clin. Microbiol. 30 (8), 2064–2070.
Hall, S.L., et al, (1992) Vir. Res. 22, 173–184.
Hall, S.L., et al, (1991) Vaccine 9, 659–667.
Brideau, R.J., et al, (1993) J. Gen. Virol. 74, 471–477.
Lehman, D.J., et al, (1993) J. Gen. Virol. 74, 459–469.
Ebata, S.N.,et al, (1992) Vir. Res. 24, 21–33.
Kasel, J.A., et al, J. Virol. 1984; 52:828–32.
Landolfi et al., Vaccine, vol. 11, Issue 4, pp. 407–414, Dec. 1992.
Takimoto et al., Journal of Virology;66,2:7597–7600, Dec. 1992.

*Primary Examiner*—Donna C. Wortman
*Assistant Examiner*—Brenda G. Brumback
*Attorney, Agent, or Firm*—Sim & McBurney

[57] ABSTRACT

In summary of this disclosure, the present invention provides hemagglutinin-neuraminidase (HN) and Fusion (F) glycoproteins isolated and purified from parainfluenza viruses types 1, 2 and 3, methods of producing the same, and uses thereof in immunogenic compositions and diagnostic embodiments. In particular, a trivalent vaccine containing HN and F glycoproteins from PIV-1, PIV-2 and PIV-3 generated an immune response capable of neutralizing each of the virus types. Modifications are possible within the scope of the invention.

9 Claims, 35 Drawing Sheets

Anti-HN Response

| Sample | Dose | Anti-HN ELISA titres $\log_2$ (titre/100)±S.D. | |
|---|---|---|---|
| | | 4 wks | 6 wks |
| HN & F | 0.3 μg | 7.8 ±1.8 | 12.6 ±0.9 |
| HN & F | 1 μg | 7.0 ±3.5 | 11.4 ±1.7 |
| HN & F | 3 μg | 9.0 ±0.0 | 13.4 ±0.9 |
| HN & F | 10 μg | 9.0 ±1.4 | 13.0 ±1.4 |
| Alum only | | 1.0 ±0.0 | 1.0 ±0.0 |

Anti-F Response

| Sample | Dose | Anti-F ELISA titres $\log_2$ (titre/100)±S.D. | |
|---|---|---|---|
| | | 4 wks | 6 wks |
| HN & F | 0.3 μg | 8.6 ±0.9 | 12.2 ±1.8 |
| HN & F | 1 μg | 8.6 ±4.6 | 11.8 ±2.3 |
| HN & F | 3 μg | 10.6 ±0.9 | 13.0 ±0.0 |
| HN & F | 10 μg | 10.6 ±0.9 | 13.0 ±1.4 |
| Alum only | | 1.0 ±0.0 | 1.0 ±0.0 |

PIV-1 Neutralization Response

| Sample | Dose | Neutralization titres $\log_2$ (titre/5)±S.D. | |
|---|---|---|---|
| | | 4 wks | 6 wks |
| HN & F | 0.3 µg | 6.4 ±0.9 | 9.0 ±0.7 |
| HN & F | 1 µg | 5.2 ±2.4 | 8.0 ±2.0 |
| HN & F | 3 µg | 7.6 ±0.6 | 9.2 ±0.8 |
| HN & F | 10 µg | 7.2 ±0.5 | 9.4 ±1.3 |
| Alum only | | 1.0 ±0.0 | 4.7 ±0.4 |

Anti-HN Response

| Sample | Dose | Anti-HN ELISA titres $\log_2$ (titre/100)±S.D. | |
|---|---|---|---|
|  |  | 4 wks | 6 wks |
| HN & F | 1 µg | 7.9 ±1.1 | 10.6 ±0.9 |
| HN & F | 10 µg | 9.2 ±0.6 | 12.6 ±0.8 |
| Control |  | 3.2 ±1.9 | 4.8 ±2.2 |

Anti-F Response

| Sample | Dose | Anti-F ELISA titres $\log_2$ (titre/100)±S.D. | |
|---|---|---|---|
| | | 4 wks | 6 wks |
| HN & F | 1 μg | 5.1 ±1.1 | 8.0 ±1.3 |
| HN & F | 10 μg | 6.7 ±0.9 | 9.6 ±0.8 |
| Control | | 1.1 ±0.3 | 1.4 ±1.0 |

PIV-1 Neutralization Response

| Sample | Dose | Neutralization titres $\log_2$ (titre/5)±S.D. | |
|---|---|---|---|
| | | 4 wks | 6 wks |
| HN & F | 1 μg | 4.0 ±0.0 | 6.8 ±0.8 |
| HN & F | 10 μg | 4.7 ±0.5 | 7.0 ±0.8 |
| Control | | 1.9 ±0.3 | 1.2 ±0.4 |

| Sample | Dose | Neutralization titres $\log_2$ (titre/5)±S.D. | |
| --- | --- | --- | --- |
| | | 4 wks | 6 wks |
| HN & F | 0.3 µg | 4.0 ±0.0 | 7.8 ±0.5 |
| HN & F | 1 µg | 4.6 ±0.9 | 9.0 ±0.7 |
| HN & F | 3 µg | 5.4 ±0.6 | 8.4 ±0.9 |
| HN & F | 10 µg | 5.2 ±0.8 | 7.2 ±0.8 |
| Alum only | | 1.0 ±0.0 | 3.3 ±0.6 |

Anti-HN Response

| Dose | HN:F Ratio | Anti-HN ELISA Titres $\log_2$ (titre/100)±S.D. | |
|---|---|---|---|
| | | 4 wks | 6 wks |
| 0.1 µg | 1:1 | 0.0 ±0.0 | 2.8 ±2.7 |
| 1 µg | 1:1 | 6.8 ±3.9 | 9.6 ±3.3 |
| 10 µg | 1:1 | 10.0 ±0.0 | 12.8 ±1.1 |
| 0.1 µg | 1:2 | 0.0 ±0.0 | 1.6 ±1.7 |
| 1 µg | 1:2 | 8.0 ±0.0 | 11.6 ±0.9 |
| 10 µg | 1:2 | 9.6 ±1.7 | 12.0 ±1.4 |
| 0.1 µg | 1:5 | 0.8 ±1.8 | 2.0 ±2.8 |
| 1 µg | 1:5 | 4.8 ±3.0 | 9.2 ±3.3 |
| 10 µg | 1:5 | 9.6 ±3.0 | 13.6 ±3.3 |
| PBS/Alum Control | N/A | 0.0 ±0.0 | 0.0 ±0.0 |

Anti-F Response

| Dose | HN:F Ratio | Anti-F ELISA Titres $\log_2$ (titre/100)±S.D. | |
|---|---|---|---|
| | | 4 wks | 6 wks |
| 0.1 µg | 1:1 | 0.8 ±1.8 | 3.6 ±4.3 |
| 1 µg | 1:1 | 7.6 ±4.8 | 11.2 ±2.3 |
| 10 µg | 1:1 | 12.8 ±1.1 | 14.4 ±0.5 |
| 0.1 µg | 1:2 | 1.2 ±2.7 | 4.0 ±2.4 |
| 1 µg | 1:2 | 8.4 ±0.9 | 12.0 ±1.4 |
| 10 µg | 1:2 | 12.4 ±0.9 | 14.8 ±0.4 |
| 0.1 µg | 1:5 | 1.6 ±3.6 | 3.2 ±4.4 |
| 1 µg | 1:5 | 7.6 ±4.3 | 12.2 ±2.4 |
| 10 µg | 1:5 | 12.4 ±4.3 | 15.6 ±2.4 |
| PBS/Alum Control | N/A | 0.0 ±0.0 | 0.0 ±0.0 |

PIV-2 Neutralization Response

| Dose | HN:F Ratio | PIV-2 Neutralization Titres $\log_2$ (titre/5)±S.D. | |
|---|---|---|---|
| | | 4 wks | 6 wks |
| 0.1 μg | 1:1 | 1.0 ±0.0 | 1.0 ±0.0 |
| 1 μg | 1:1 | 2.8 ±1.6 | ≥6.0 |
| 10 μg | 1:1 | ≥6.8 | ≥8.0 |
| 0.1 μg | 1:2 | 1.0 ±0.0 | 1.0 ±0.0 |
| 1 μg | 1:2 | 1.6 ±0.9 | ≥8.0 |
| 10 μg | 1:2 | 3.8 ±0.8 | ≥8.0 |
| 0.1 μg | 1:5 | 1.0 ±0.0 | 1.0 ±0.0 |
| 1 μg | 1:5 | 1.2 ±0.4 | ≥5.4 |
| 10 μg | 1:5 | ≥6.0 | ≥8.0 |
| PBS/Alum Control | N/A | 1.0 ±0.0 | 1.0 ±0.0 |

PIV-2 Hemagglutination Inhibition (HAI) Titres

| Dose | HN:F Ratio | PIV-2 HAI Titres $\log_2$ (titre/5)±S.D. | |
|---|---|---|---|
| | | 4 wks | 6 wks |
| 0.1 μg | 1:1 | 1.0 ±0.0 | 1.2 ±0.5 |
| 1 μg | 1:1 | 4.0 ±1.9 | 6.8 ±2.3 |
| 10 μg | 1:1 | 6.0 ±0.0 | 9.6 ±0.9 |
| 0.1 μg | 1:2 | 1.0 ±0.0 | 1.6 ±0.9 |
| 1 μg | 1:2 | 3.6 ±1.5 | 7.4 ±0.6 |
| 10 μg | 1:2 | 5.6 ±1.1 | 8.8 ±0.8 |
| 0.1 μg | 1:5 | 1.0 ±0.0 | 1.0 ±0.0 |
| 1 μg | 1:5 | 1.8 ±1.1 | 4.6 ±3.3 |
| 10 μg | 1:5 | 6.2 ±1.3 | 9.2 ±0.5 |
| PBS/Alum Control | N/A | 1.0 ±0.0 | 1.0 ±0.0 |

Anti-PIV-3 ELISA Titres

| Sample | Dose μg | EIA Titres $\log_2$ (EIA/100)±SE | |
|---|---|---|---|
| | | 5 wks | 7 wks |
| HN & F | 1.0 | 9.4 ±0.8 | 13.8 ±1.6 |
| HN & F | 3.0 | 11.0 ±1.3 | 14.6 ±0.8 |
| HN & F | 10.0 | 11.0 ±0.0 | 15.0 ±0.0 |
| HN & F | 20.0 | 11.4 ±0.8 | 15.0 ±0.0 |
| PIV3 | $10^5 TCID_{50}$ | 7.0 ±1.3 | 8.6 ±0.8 |
| Control | | 3.4 ±2.0 | 4.6 ±2.7 |

Hemagglutination-Inhibition Titres

| Sample | Dose µg | HI Titres log$_2$ (HI/5)±SE | |
|---|---|---|---|
| | | 5 wks | 7 wks |
| HN & F | 1.0 | 7.2 ±0.6 | 11.8 ±0.4 |
| HN & F | 3.0 | 7.4 ±1.4 | 11.0 ±0.6 |
| HN & F | 10.0 | 7.0 ±0.6 | 11.4 ±0.5 |
| HN & F | 20.0 | 8.6 ±0.8 | 11.8 ±0.4 |
| PIV3 | $10^5 TCID_{50}$ | 5.6 ±1.2 | 7.1 ±1.3 |
| Control | | 1.0 ±0.0 | 1.0 ±0.0 |

Neutralization Titres

| Sample | Dose μg | NT Titres $\log_2$(NT/5)±SE | |
|---|---|---|---|
| | | 5 wks | 7 wks |
| HN & F | 1.0 | 4.8 ±0.7 | 10.4 ±1.2 |
| HN & F | 3.0 | 5.0 ±0.9 | 10.0 ±0.0 |
| HN & F | 10.0 | 5.4 ±0.8 | 10.2 ±0.4 |
| HN & F | 20.0 | 6.0 ±0.0 | 11.0 ±0.9 |
| PIV3 | $10^5$ TCID$_{50}$ | 3.0 ±1.4 | 5.6 ±1.9 |
| Control | | 1.0 ±0.0 | 1.0 ±0.0 |

Anti-PIV-3 ELISA Titres

| Sample | Dose μg | EIA Titres $\log_2$ (EIA/5)±SE | |
|---|---|---|---|
| | | 4 wks | 6 wks |
| HN & F | 1.0 | 7.8 ±1.0 | 12.2 ±1.0 |
| HN & F | 3.0 | 9.4 ±1.5 | 13.4 ±0.8 |
| HN & F | 10.0 | 9.4 ±0.8 | 13.0 ±1.3 |
| HN & F | 20.0 | 10.2 ±1.0 | 13.8 ±1.0 |
| PIV-3 | $10^5 TCID_{50}$ | 9.4 ±0.8 | 10.6 ±0.8 |
| Control | | 1.0 ±0.0 | 1.0 ±0.0 |

Hemagglutination-Inhibition Titres

| Sample | Dose | HI Titres log$_2$ (HI/5)±SE | |
|---|---|---|---|
| | µg | 4 wks | 6 wks |
| HN & F | 1.0 | 4.2 ±1.6 | 10.4 ±0.8 |
| HN & F | 3.0 | 6.4 ±1.0 | 11.2 ±0.4 |
| HN & F | 10.0 | 6.8 ±04 | 11.0 ±0.6 |
| HN & F | 20.0 | 7.0 ±0.0 | 11.6 ±0.5 |
| PIV-3 | 10$^5$TCID$_{50}$ | 4.8 ±1.0 | 7.6 ±0.8 |
| Control | | 1.0 ±0.0 | 1.0 ±0.0 |

Neutralization Titres

| Sample | Dose μg | NT Titres $\log_2$ (NT/5)±SE | |
|---|---|---|---|
| | | 4 wks | 6 wks |
| HN & F | 1.0 | 2.0 ±0.4 | 9.0 ±0.0 |
| HN & F | 3.0 | 4.6 ±1.6 | 8.8 ±0.4 |
| HN & F | 10.0 | 4.6 ±0.8 | 8.0 ±0.0 |
| HN & F | 20.0 | 5.0 ±0.0 | 8.4 ±0.8 |
| PIV-3 | $10^5 TCID_{50}$ | 2.8 ±1.2 | 6.4 ±1.0 |
| Control | | 1.0 ±0.0 | 1.0 ±0.0 |

Anti-PIV-3 ELISA Titres

| Sample | Dose μg | EIA Titres $\log_2$ (EIA/5)±SE 4 wks |
|---|---|---|
| HN & F | 1.0 | 9.4 ±0.8 |
| HN & F | 3.0 | 10.2 ±1.0 |
| HN & F | 10.0 | 9.0 ±0.0 |
| HN & F | 20.0 | 10.2 ±1.6 |
| PIV-3 | $10^5 TCID_{50}$ | 11.0 ±0.0 |
| Control | | 1.0 ±0.0 |

Hemagglutination-Inhibition Titres

| Sample | Dose μg | HI Titres $\log_2 (HI/5) \pm SE$ 4 wks |
|---|---|---|
| HN & F | 1.0 | 5.6 ±0.8 |
| HN & F | 3.0 | 5.2 ±0.4 |
| HN & F | 10.0 | 4.4 ±1.7 |
| HN & F | 20.0 | 6.8 ±0.4 |
| PIV-3 | $10^5 TCID_{50}$ | 6.0 ±0.0 |
| Control | | 1.0 ±0.0 |

Neutralization Titres

| Sample | Dose μg | NT Titres $\log_2$ (NT/5)±SE |
|---|---|---|
| | | 4 wks |
| HN &F | 1.0 | 4.2 ±0.7 |
| HN &F | 3.0 | 4.8 ±0.4 |
| HN &F | 10.0 | 5.2 ±0.7 |
| HN &F | 20.0 | 4.8 ±0.8 |
| PIV-3 | $10^5 TCID_{50}$ | 5.4 ±0.5 |
| Control | | 1.0 ±0.0 |

| Sample | Dose μg | Virus Titres $\log_{10}$ (TCID50/ml)±SE | |
|---|---|---|---|
| | | Nasal Washes | Lung Lavages |
| HN & F | 1.0 | 2.22 ±0.87 | 2.5 ±0.0 |
| HN & F | 3.0 | 1.96 ±0.47 | 2.5 ±0.0 |
| HN & F | 10.0 | 1.72 ±0.31 | 2.5 ±0.0 |
| HN & F | 20.0 | 1.88 ±0.32 | 1.6 ±0.2 |
| PIV-3 | $10^5$ TCID$_{50}$ | 1.50 ±0.00 | 2.1 ±0.4 |
| Control | | 5.24 ±0.26 | 3.9 ±1.0 |

Hemagglutination-Inhibition Titres

| Sample | HI Titres $\log_2 /0.05\text{ml}) \pm SD$ | |
|---|---|---|
| | 4 wks | 6 wks |
| HN &F-1 μg | 9.3 ±0.6 | 10.7 ±0.0 |
| PIV-3 | 7.0 ±0.0 | 8.5 ±0.0 |
| Control | <3 | 2.8 ±1.0 |

Neutralization Titres

| Sample | NT Titres log$_2$ /0.05ml)±SD | |
|---|---|---|
| | 4 wks | 6 wks |
| HN &F-1 μg | 9.2 ±0.6 | 11.5 ±0.0 |
| PIV-3 | 9.8 ±0.0 | 11.5 ±0.0 |
| Control | <3 | 2.8 ±1.0 |

Virus Lung Titres after PIV-3 Challenge

| Sample | Virus Titres log$_{10}$ (TCID50)/g |
|---|---|
| | |
| HN &F-1 µg | 0.00 ±0.0 |
| PIV-3 | 0.00 ±0.0 |
| Control | 3.4 ±0.3 |

FIG.

PIV-1 Neutralization Response

| Sample | Dose | PIV-1 Neutralization titres $\log_2$ (titre/5)±SD | |
|---|---|---|---|
| | | 4 wks | 6 wks |
| HN & F | 0.3 µg | 4.0 ±1.2 | 6.4 ±0.9 |
| HN & F | 1 µg | 4.4 ±0.6 | 7.2 ±0.8 |
| HN & F | 3 µg | 4.8 ±0.8 | 6.6 ±0.6 |
| HN & F | 10 µg | 5.6 ±0.6 | 7.4 ±0.6 |
| Alum only | | 1.0 ±0.0 | 4.7 ±0.4 |

PIV-2 Neutralization Response

| Sample | Dose | PIV-2 Neutralization titres $\log_2$ (titre/5)±SD | |
|---|---|---|---|
| | | 4 wks | 6 wks |
| HN & F | 0.3 µg | 4.0 ±0.7 | 7.4 ±0.6 |
| HN & F | 1 µg | 4.2 ±0.5 | 8.0 ±0.0 |
| HN & F | 3 µg | 5.0 ±1.2 | 8.0 ±1.0 |
| HN & F | 10 µg | 6.0 ±0.0 | 8.6 ±0.6 |
| Alum only | | 1.0 ±0.0 | 3.3 ±0.4 |

PIV-3 Neutralization Response

| Sample | Dose | PIV-3 Neutralization titres $\log_2$ (titre/5)±SD | |
|---|---|---|---|
| | | 4 wks | 6 wks |
| HN & F | 0.3 µg | 3.4 ±0.9 | 9.0 ±1.0 |
| HN & F | 1 µg | 3.0 ±1.9 | 7.2 ±3.0 |
| HN & F | 3 µg | 3.4 ±0.6 | 8.2 ±1.5 |
| HN & F | 10 µg | 3.6 ±1.7 | 10.0 ±1.0 |
| Alum only | | 1.0 ±0.0 | 1.0 ±0.0 |

PARAINFLUENZA VIRUS GLYCOPROTEINS AND VACCINES

FIELD OF INVENTION

The present invention relates to parainfluenza virus (PIV) glycoproteins, methods of preparation of the same and multivalent vaccine compositions comprising such proteins.

BACKGROUND OF THE INVENTION

Human respiratory syncytial viruses, subtypes A and B (RSV A&B) and human parainfluenza virus types 1,2 and 3 (PIV-1,2,3) infections are the most common causes of acute lower respiratory tract infection in infants and children in the developed world. In the United States alone, close to 5 million children per year will be infected with the parainfluenza viruses. PIV-3 is second only to RSV as the major causative agent of bronchiolitis and pneumonia in infants. It is estimated that in the United States, approximately 600,000 children under the age of 6 develop laryngo-tracheobronchitis (croup) each year as a result of infection with PIV-1 and 2 and that approximately 1,000 infants may die as a result of PIV-3 infection. Approximately 10 to 15% of hospitalizations with bronchiolitis and pneumonia can be attributed to infection with PIV-3 with greater than 1.4 million infants in the United States suffering a clinically significant PIV-3 infection each year (ref. 1 -Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Of those infected with PIV-3, 1 to 2% will require hospitalization and some children will die. The peak age for PIV-3 infections occurs at 2 to 4 months of age while PIV-associated croup peaks between 9 to 24 months of age. Reinfections are very common with the parainfluenza viruses, occurring most frequently with PIV-3.

Currently, safe and effective vaccines capable of protecting infants and young children from these viral infections are not available. Therefore, development of an effective parainfluenza vaccine is a priority.

Studies on the development of live viral vaccines and glycoprotein subunit vaccines against parainfluenza virus infection are being pursued. Clinical trial results with a formalin-inactivated PIV types 1,2,3 vaccine demonstrated that this vaccine was not efficacious (refs. 2, 3, 4). Further development of chemically-inactivated vaccines was discontinued after clinical trials with a formalin-inactivated RSV vaccine demonstrated that not only was the vaccine not effective in preventing RSV infection but many of the vaccinees who later became infected with RSV suffered a more serious disease. Most of parainfluenza vaccine research has focussed on candidate PIV-3 vaccines (ref. 5) with significantly less work being reported for PIV-1 and PIV-2. Recent approaches to PIV-3 vaccines have included the use of the closely related bovine parainfluenza virus type 3 and the generation of attenuated viruses by cold-adaptation of the virus (refs. 6, 7, 8, 9).

Another approach to parainfluenza virus type 3 vaccine development is a subunit approach focusing on the surface glycoproteins hemagglutinin-neuraminidase (HN) and the fusion (F) protein (refs. 10, 11, 12). The HN antigen, a typical type II glycoprotein, exhibits both haemagglutination and neuraminidase activities and is responsible for the attachment of the virus to sialic acid containing host cell receptors. The type I F glycoprotein mediates fusion of the viral envelope with the cell membrane as well as cell to cell spread of the virus. It has recently been demonstrated that both the HN and F glycoproteins are required for membrane fusion. The F glycoprotein is synthesized as an inactive precursor (F) which is proteolytically cleaved into disulfide-linked F2 and F1 moieties. While the HN and F proteins of PIV-1, 2 and 3 are structurally similar, they are antigenically distinct. Neutralizing antibodies against the HN and F proteins of one of PIV type are not cross-protective. Thus, an effective PIV subunit vaccine must contain the HN and F glycoproteins from the three different types of parainfluenza viruses. Antibody to either glycoprotein is neutralizing in vitro. A direct correlation has been observed between the level of neutralizing antibody titres and resistance to PIV-3 infections in infants. Native subunit vaccines for parainfluenza virus type 3 have investigated the protectiveness of the two surface glycoproteins. Typically, the glycoproteins are extracted from virus using non-ionic detergents and further purified using lectin affinity or immunoaffinity chromatographic methods. However, neither of these techniques may be entirely suitable for large scale production of vaccines under all circumstances. In small animal protection models (hamsters and cotton rats), immunization with the glycoproteins was demonstrated to prevent infection with live PIV-3 (refs. 13, 14, 15, 16, 17). The HN and F glycoproteins of PIV-3 have also been produced using recombinant DNA technology. HN and F glycoproteins have been produced in insect cells using the baculovirus expression system and by use of vaccinia virus and adenovirus recombinants (refs. 18, 19, 20, 21, 22). In the baculovirus expression system, both full-length and truncated forms of the PIV-3 glycoproteins as well as a chimeric F-HN fusion protein have been expressed. The recombinant proteins have been demonstrated to be protective in small animal models (see WO 91/00104, U.S. application Ser. No. 07/773,949 filed Nov. 29, 1991, assigned to the assignee hereof).

Parainfluenza virus infection may lead to serious disease. It would be advantageous to provide purified PIV glycoproteins and methods for their purification from native virus for use as antigens in immunogenic preparations including vaccines, carriers for other antigens and immunogens and the generation of diagnostic reagents.

SUMMARY OF THE INVENTION

The present invention provides the production of PIV-3 on a vaccine quality cell line (VERO cells), purification of the virus from fermentor harvests, extraction of the HN and F glycoproteins from the purified virus and copurification of the HN and F glycoproteins to a purity of up to or greater than about 85% without involving immunoaffinity or lectin affinity steps. In particular the lectin affinity procedure could lead to leaching of the ligand into the product.

In addition, there is provided, for the first time, procedures for the isolation and purification of the HN and F glycoproteins of PIV-1 and PIV-2 and also immunogenic compositions comprising mixtures of the isolated and purified HN and F glycoproteins of PIV-1, PIV-2 and PIV-3.

The isolated and purified HN and F glycoproteins are non-pyrogenic, non-immunopotentiating, and essentially free of serum and cell-line contaminants. The isolated and purified glycoproteins are immunogenic, free of any infectious PIV and other adventitious agents.

Accordingly, in one aspect of the present invention, there is provided an isolated and purified hemagglutinin-neuraminidase (HN) glycoprotein of parainfluenza virus type 1 (PIV-1), generally having an apparent molecular mass of about 70 to about 80 kDa, as determined by sodium dodecyl sulphate polyacrylamide gel electrophoresis (SDS-PAGE) under reducing conditions, or a fragment or an analog thereof retaining the immunological properties of the glycoprotein.

In another aspect of the present invention, there is provided an isolated and purified fusion (F) glycoprotein of parainfluenza virus type 1 (PIV-l), generally having an apparent molecular mass of the $F_1$ polypeptide subunit of about 45 to about 55 kDa, as determined by sodium dodecyl sulphate polyacrylamide gel electrophoresis (SDS-PAGE) under reducing conditions, or a fragment or an analog thereof retaining the immunological properties of the glycoprotein.

A further aspect of the invention provides a coisolated and copurified mixture of glycoproteins of parainfluenza virus type 1 (PIV-1) consisting essentially of the hemagglutinin-neuraminidase (HN) glycoprotein, generally having an apparent molecular mass of about 70 to about 80 kDa and the fusion (F) glycoprotein having an apparent molecular mass of the $F_1$ polypeptide subunit of about 45 to about 55 kDa, wherein the molecular masses are determined by sodium dodecyl sulfate polyacrylamide gel electrophoresis (SDS-PAGE) under reducing conditions. Such mixture preferably is at least about 75% pure.

In an additional aspect of the invention, there is provided an isolated and purified hemagglutinin-neuraminidase (HN) glycoprotein of parainfluenza virus type 2 (PIV-2), generally having an apparent molecular mass of about 75 to about 85 kDa, as determined by sodium dodecyl sulphate polyacrylamide gel electrophoresis (SDS-PAGE) under reducing conditions, or a fragment or an analog thereof retaining the immunological properties of said glycoprotein. The HN glycoprotein may be isolated substantially free of the fusion (F) glycoprotein of PIV-2 and preferably may be at least about 65% pure.

A yet further aspect of the present invention provides an isolated and purified fusion (F) glycoprotein of parainfluenza virus type 2 (PIV-2) generally having an apparent molecular mass of the $F_1$ polypeptide subunit of about 45 to about 55 kDa, as determined by sodium dodecyl sulphate polyacrylamide gel electrophoresis (SDS-PAGE) under reducing conditions, or a fragment or an analog thereof retaining the immunological properties of said glycoprotein. The F glycoprotein may be isolated substantially free of the HN glycoprotein of PIV-2 and preferably may be at least about 80% pure.

In a further aspect of the present invention, there is provided a coisolated and copurified mixture of undenatured glycoproteins of parainfluenza virus type 3 (PIV-3) free from lectin and consisting essentially of the hemagglutinin-neuraminidase (HN) glycoprotein, generally having an apparent molecular mass of about 70 to about 75 kDa and the fusion (F) glycoprotein having an apparent molecular mass of about 45 to about 50 kDa, wherein the molecular masses are determined by sodium dodecyl sulfate polyacrylamide gel electrophoresis (SDS-PAGE) under reducing conditions. The mixture is preferably at least about 75% pure.

The present invention also includes multivalent immunogenic compositions comprising glycoproteins from PIV-1, PIV-2 and PIV-3. Accordingly, in an additional aspect of the present invention, there is provided an immunogenic composition, comprising immunoeffective amounts of: (a) the hemagglutinin-neuraminidase (HN) glycoprotein of parainfluenza virus type 1 (PIV-1), generally having an apparent molecular mass of about 70 to about 80 kDa; (b) the fusion (F) glycoprotein of parainfluenza virus type 1 (PIV-1), generally having an apparent molecular mass of the $F_1$ polypeptide subunit of about 45 to about 55 kDa; (c) the hemagglutinin-neuraminidase (HN) glycoprotein of parainfluenza virus type 2 (PIV-2), generally having an apparent molecular mass of about 75 to about 85 kDa; (d) the fusion (F) glycoprotein of parainfluenza virus type 2 (PIV-2), generally having an apparent molecular mass of the $F_1$ polypeptide subunit of about 45 to about 55 kDa; (e) the hemagglutinin-neuraminidase (HN) glycoprotein of parainfluenza virus type 3 (PIV-3), generally having an apparent molecular mass of about 70 to about 80 kDa; and (f) the fusion (F) glycoprotein of parainfluenza virus type 3 (PIV-3), generally having an apparent molecular mass of the $F_1$ polypeptide subunit of about 45 to about 55 kDa; or fragments or analogs of any respective one of the glycoproteins (a) to (f) which retains the immunological properties of said glycoprotein; wherein the molecular masses are determined by sodium dodecyl sulfate polyacrylamide gel electrophoresis (SDS-PAGE) under reducing conditions.

The HN and F glycoproteins of PIV-1 and PIV-3 preferably are provided as a coisolated and copurified mixture of the glycoproteins and the HN and F glycoproteins of PIV-2 are preferably provided as separately isolated and purified glycoproteins.

The immunogenic compositions provided herein may be formulated as a vaccine with preselected amounts of each of the glycoproteins for in vivo administration to a host, which may be a primate, specifically a human host, to confer protection against disease caused by PIV-1, PIV-2 and PIV-3.

The immunogenic compositions of the invention may be formulated as a microparticle, capsule, ISCOM or liposome preparation. The immunogenic composition may be employed in combination with a targeting molecule for delivery to specific cells of the immune system or to mucosal surfaces. Some targetting molecules include strain B12 and fragments of bacterial toxins, as described in WO 92/17167 (Biotech Australia Pty. Ltd.), and monoclonal antibodies, as described in U.S. Pat. No. 5,194,254 (Barber et al). The immunogenic compositions may further comprise at least one other immunogenic or immunostimulating material, which may be at least one adjuvant.

The at least one adjuvant may be selected from the group consisting of aluminum phosphate, aluminum hydroxide, QS21, Quil A, derivatives and components thereof, ISCOM matrix, calcium phosphate, calcium hydroxide, zinc hydroxide, a glycolipid analog, an octodecyl ester of an amino acid, a muramyl dipeptide, polyphosphazene and a lipoprotein, and other adjuvants to induce a Th1 response.

The immunogenic compositions provided herein may be formulated to comprise at least one additional immunogen, which conveniently may comprise a human respiratory syncytial virus (RSV) protein from RSV types A and/or B. However, other immunogens, such as from Chlamydia, polio, hepatitis B, diphtheria toxoid, tetanus toxiod, influenza, haemophilus, pertussis, pneumococcal, mycobacterial, hepatitis A, Moraxella may be incorporated into the compositions.

The present invention extends to the copurification and coisolation of HN and F glycoproteins from parainfluenza viruses as well as HN and F proteins individually.

An additional aspect of the present invention provides a method of generating an immune response in a host by administering thereto an immunoeffective amount of the immunogenic composition provided herein. Preferably, the immunogenic composition is formulated as a vaccine for in vivo administration to the host and the administration to the host, including humans, confers protection against disease caused by PIV-1, PIV-2 and PIV-3. The immune response may be humoral or a cell-mediated immune response.

The present invention provides, in an additional aspect thereof, a method of producing a vaccine for protection against disease caused by parainfluenza virus (PIV) infection, comprising administering the immunogenic composition provided herein to a test host to determine the relative amounts of the components thereof and a frequency of administration thereof to confer protection against disease caused by a PIV-1, PIV-2 and PIV-3; and formulating the immunogenic composition in a form suitable for administration to a treated host in accordance with said determined amount and frequency of administration. The treated host may be a human.

A further aspect of the invention provides a method of determining the presence in a sample of antibodies specifically reactive with a glycoprotein of parafluenza virus (PIV), comprising the steps of:

(a) contacting the sample with the immunogenic composition as provided herein to produce complexes comprising a parainfluenza virus glycoprotein and any said antibodies present in the sample specifically reactive therewith; and (b) determining production of the complexes.

In a further aspect of the invention, there is provided a method of determining the presence in a sample of a glycoprotein of parainfluenza virus (PIV) comprising the steps of:

(a) immunizing a subject with the immunogenic composition as provided herein, to produce antibodies specific for the HN and F glycoproteins of PIV-1, PIV-2 and PIV-3;

(b) contacting the sample with the antibodies to produce complexes comprising any PIV glycoprotein present in the sample and the glycoprotein specific antibodies; and (c) determining production of the complexes.

A further aspect of the invention provides a diagnostic kit for determining the presence of antibodies in a sample specifically reactive with a glycoprotein of parainfluenza virus, comprising:

(a) an immunogenic composition as provided herein;

(b) means for contacting the immunogenic composition with the sample to produce complexes comprising a parainfluenza virus glycoprotein and any said antibodies present in the sample; and (c) means for determining production of the complexes.

The invention also provides a diagnostic kit for detecting the presence, in a sample, of a glycoprotein of parainfluenza virus (PIV), comprising:

(a) antibodies specific for the HN and F glycoproteins of PIV-1, PIV-2 and PIV-3;

(b) means for contacting the antibodies with the sample to produce complexes comprising the PIV glycoprotein and PIV glycoprotein- specific antibodies; and (c) means for determining production of the complex.

In an additional aspect of the invention, there is provided a method of producing monoclonal antibodies specific for glycoproteins of parainfluenza virus (PIV), comprising:

(a) administrating an immunogenic composition as provided herein to at least one mouse to produce at least one immunized mouse, (b) removing B-lymphocytes from the at least one immunized mouse;

(c) fusing the B-lymphocytes from the at least one immunized mouse with myeloma cells, thereby producing hybridomas;

(d) cloning the hybridomas which produce a selected anti-PIV glycoprotein antibody;

(e) culturing the anti-PIV glycoprotein antibody-producing clones; and (f) isolating anti-PIV glycoprotein antibodies from the cultures.

The present invention, in a further aspect, provides a method of producing a coisolated and copurified mixture of glycoproteins of parainfluenza virus type 1 (PIV-1), which comprises growing PIV-1 in a culture medium, separating the grown virus from the culture medium, solubilizing the hemagglutinin-neuraminidase (HN) and the fusion (F) envelope glycoproteins from the separated virus; and coisolating and copurifying the solubilized envelope glycoproteins.

The coisolation and copurification may be effected by collecting HN and F glycoprotein-containing flow-through from ion exchange chromatography of the solubilized envelope glycoproteins; loading the flow through onto a hydroxyapatite matrix, and selectively coeluting the HN and F glycoproteins from the hydroxyapatite matrix. The selectively eluted HN and F glycoproteins may be further concentrated by tangential flow ultrafiltration. The coisolation and copurification may further comprise selectively coprecipitating the HN and F glycoproteins, separating the coprecipitated HN and F glycoproteins and resolubilizing the separated HN and F glycoproteins.

An additional aspect of the present invention provides a method of producing an isolated and purified individual glycoprotein of parainfluenza virus type 2 (PIV-2), which comprises growing PIV-2 in a culture medium; separating the grown virus from the culture medium; solubilizing the hemagglutinin-neuraminidase (HN) and the fusion (F) envelope glycoproteins from the separated virus; and isolating and purifying at least one of the solubilized envelope glycoproteins.

The solubilized envelope glycoproteins are separately isolated and purified. Such separate isolation and purification may be effected by collecting F glycoprotein-containing flow-through from ion exchange chromatography of the solubilized envelope glycoproteins while HN glycoprotein is retained on the ion exchange medium; applying the collected flow through to a hydroxyapatite matrix and collecting an F glycoprotein-containing flow through, selectively removing detergent used in the solubilization step from the hydroxyapatite matrix flow through to provide isolated and purified F glycoprotein, and eluting HN glycoprotein from the ion exchange medium to provide isolated and purified HN glycoprotein. Nucleic acid contaminants may be removed from the isolated and purified HN glycoprotein by treatment with a nuclease including Benzonase (TM). The isolated and purified HN glycoprotein may be applied to a gel filtration medium and the HN glycoprotein subsequently collected therefrom to separate the HN glycoprotein from contaminants of other molecular weights. Alternatively, the isolated and purified HN glycoprotein may be applied to a hydroxyapatite matrix to bind HN glycoprotein to the matrix and the HN glycoprotein is subsequently eluted therefrom. The isolated and purified F and HN glycoproteins may be subsequently concentrated by tangential flow ultrafiltration.

The present invention additionally includes a method of producing coisolated and copurified glycoproteins of parainfluenza virus type 3 (PIV-3), which comprises growing PIV-3 in a culture medium, separating the grown virus from the culture medium, solubilizing the hemagglutinin-neuraminidase (HN) and the fusion (F) envelope glycoproteins from the separated virus, and coisolating and copurifying the solubilized glycoproteins free from lectin.

The coisolating and copurifying may be effected by loading HN and F glycoproteins on a first ion-exchange medium while permitting contaminants to pass through the medium, coeluting the HN and F glycoproteins from the first ion-exchange medium, to separate the HN glycoprotein from contaminants of other molecular weights. The coeluted HN and F glycoproteins are applied to a second ion-exchange medium while allowing contaminants to pass through the second ion-exchange medium. The HN and F glycoproteins are subsequently coeluted therefrom, to provide the coisolated and copurified HN and F glycoproteins. The coeluted HN and F glycoproteins may be concentrated by tangential flow ultrafiltration.

Advantages of the present invention include:

isolated and purified HN and F glycoproteins of PIV-1, PIV-2 and PIV-3 multivalent immunogenic compositions containing such glycoproteins procedures for isolating such glycoprotein diagnostic kits for identification of PIV and, hosts infected thereby.

BRIEF DESCRIPTION OF DRAWINGS

The present invention will be further understood from the following description with reference to the Figures, in which:

FIGS. 14(e) and 14(f) show the PIV-3 lung titres in cotton rats immunized with purified parainfluenza type 3 HN and F glycoproteins and challenged with live PIV-3;

GENERAL DESCRIPTION OF INVENTION

Figure 1:
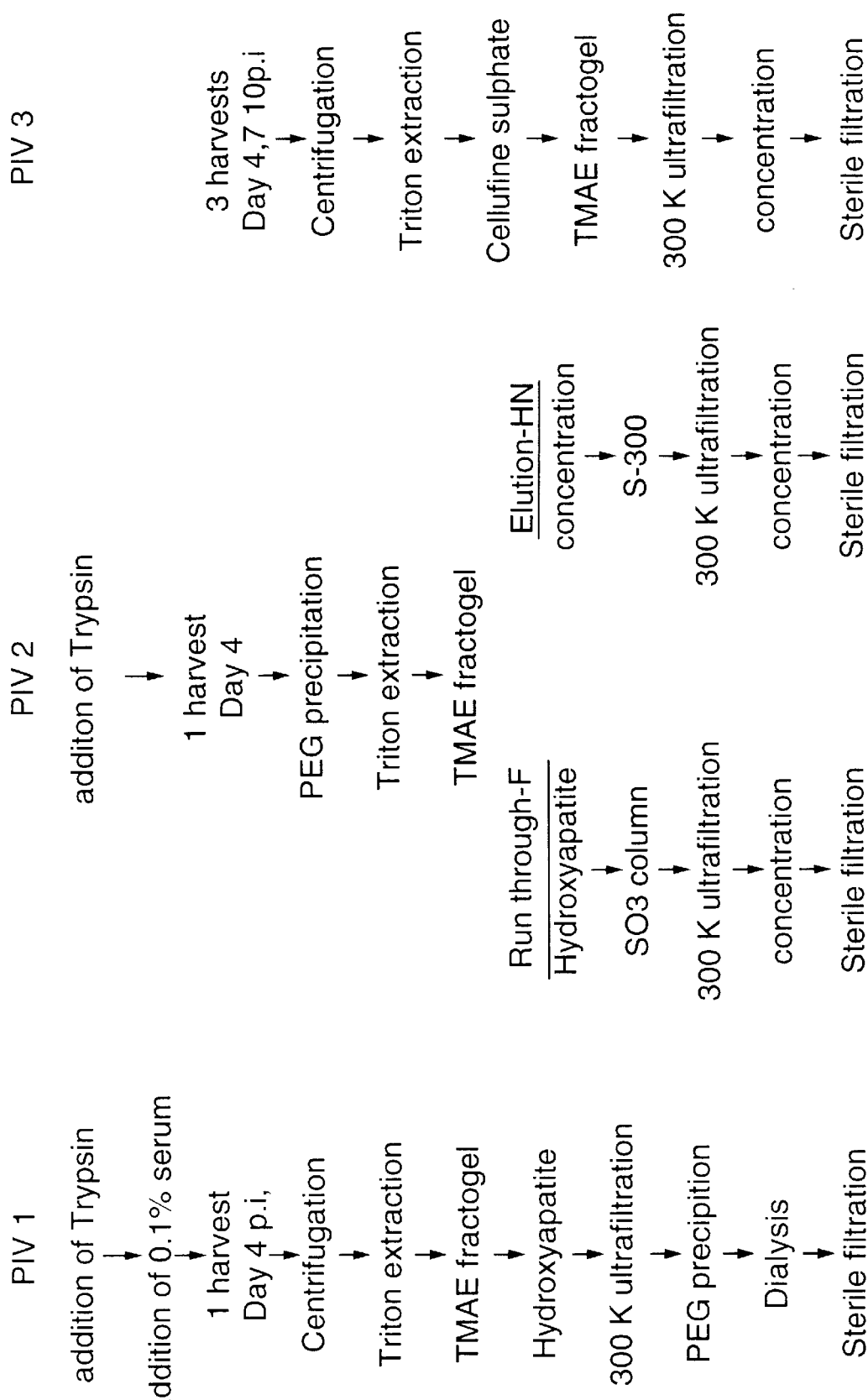
FIG. 1 is a flow diagram of a method of purifying hemagglutinin-neuraminidase (HN) and Fusion (F) glycoproteins from parainfluenza viruses types 1, 2 and 3 according to particular embodiments of the invention.

As discussed above, the present invention includes coisolated and copurified HN and F glycoproteins of PIV-1 from virus. As schematically seen in FIG. 1 for PIV-1, the virus is grown on a vaccine quality cell line, such as VERO cells, and the grown virus is harvested. The fermentation may be effected in the presence of fetal bovine serum (FBS) and trypsin.

The viral harvest is filtered and then concentrated typically using tangential flow ultrafiltration using a membrane of desired molecular weight cut-off and diafiltered. The virus harvest concentrate may be centrifuged and the supernatant discarded. The pellet from the centrifugation then is detergent extracted to solubilize the HN and F glycoproteins, for example, by resuspending the pellet to the original harvest concentrate volume in an extraction buffer containing a detergent such as a non-ionic detergent including TRITON X-100.

Following centrifugation to remove non-soluble proteins, the HN and F glycoprotein extract is purified by chromatographic procedures. The extract may first be applied to an ion exchange chromatography column such as a TMAE-fractogel column equilibrated to permit the HN and F glycoproteins to flow through while impurities are retained on the column.

Next, the flow through may be loaded onto a hydroxyapatite column, equilibrated to permit binding of the HN and F glycoproteins to the matrix and to permit contaminants to pass from the column. The bound HN and F glycoproteins then are coeluted from the column by a suitable elutant. The resulting copurified solution of HN and F glycoproteins may be further processed to increase its purity.

The eluate first may be concentrated by tangential flow ultrafiltration using a membrane of desired molecular weight cut-off. The filtrate may be contacted with a polyethylene glycol of desired molecular weight, for example, about 6000 to 8000, to precipitate the glycoprotein. Following centrifugation and discard of the supernatant, the pellet may be resuspended in PBS and dialyzed to remove the polyethylene glycol. Finally, the dialyzed solution of HN and F glycoproteins of PIV-1 may be sterile filtered. The sterile filtered solution may be adsorbed onto alum.

The polyethylene glycol precipitation and resuspension purification step may be effected at an earlier stage of the purification operation, if desired.

The HN and F glycoproteins of PIV-2 are recovered as individual proteins from the PIV-2 virus, following the scheme generally shown in FIG. 1. Following growth and harvesting of the virus, a virus harvest concentrate is provided in similar manner to PIV-1. The virus harvest concentrate may be contacted with a polyethylene glycol to precipitate the virus suspension. Following centrifugation and discard of the supernatant, the pellet is resuspended in a solution of urea before again centrifuging and discard of the supernatant.

The pellet is resuspended and the resulting urea-washed virus suspension is contacted with detergent to solubilize the HN and F glycoproteins of PIV-2 from the cell mass. Following centrifugation, the supernatant is recovered to further purification of the glycoproteins and the non-soluble proteins discarded.

The supernatant may be applied to an ion exchange chromatography column, such as a TMAE-fractogel column, suitably equilibrated to permit the F glycoprotein to run through the column while the HN protein is retained on the column, thereby effectively separating the two proteins, which then are separately processed.

The run through from the ion exchange column may be loaded onto a hydroxyapatite matrix suitably equilibrated to permit the F glycoprotein to flow through the column while contaminants are retained on the column. The flow through then may be applied to a further ion exchange column suitably equilibrated to permit the F glycoprotein to be retained on the column while contaminants flow through the column.

The F-glycoprotein then may be eluted from the column to provide a purified solution of the PIV-2 F glycoprotein. The eluate may be concentrated by tangential flow ultrafiltration using a membrane of desired molecular weight cut-off. The concentrated F-glycoprotein solution may be sterile filtered.

The HN glycoprotein of PIV-2 is eluted from the ion-exchange column under suitable conditions. The eluate then may be passed through a gel filtration column, such as a Sephacryl S-300 column, to separate the HN glycoprotein from contaminants of other molecular weights. A hydroxyapatite column may be employed in place of the Sephacryl column.

The HN glycoprotein may be eluted from the column to provide a purified solution of PIV-2 HN glycoprotein. The eluate may be concentrated by tangential flow ultrafiltration using a membrane of desired molecular weight cut-off. The concentrated HN-glycoprotein solution may be sterile filtered.

The PIV-3 HN and F glycoproteins are coisolated and copurified from the PIV-3 virus following the scheme generally shown in FIG. 1. The virus is grown on a cell line of vaccine quality and the grown virus is harvested, in a single or multiple harvestings. Such multiple harvesting may be taken, for example, on days 4, 7 and 10 post-infection.

The viral harvests may be concentrated by ultrafiltration. The concentrated viral harvests may be subjected to an initial purification operation, for example, by gel filtration chromatography, polyethylene glycol precipitation or Cellufine sulfate chromatography. The purified virus may then be detergent extracted to solubilize the HN and F glycoproteins.

Following solubilization of the HN and F glycoproteins of PIV-3, the supernatant may be loaded onto an ion-exchange column such as Cellufine sulfate chromatography column equilibrated to permit the glycoproteins to bind to the column while permitting contaminants to flow through. Similarly, a TMAE-fractogel column may be used in place of the Cellufine sulfate column. The two columns also may be combined in sequential purification steps.

The HN and F glycoproteins are coeluted from the columns to provide a copurified solution of the glycoproteins. This solution may be concentrated by tangential flow ultrafiltration using a membrane of desired molecular weight cut-off and diafiltered. The concentrated glycoprotein preparation may be sterile filtered and adsorbed onto column.

The purified HN and F glycoproteins may be in the form of homo and hetero oligomers including dimers, tetramers and higher species.

The PIV glycoprotein preparations demonstrated no evidence of any adventitious agent, hemadsorbing agent or live virus.

The invention extends to HN and F glycoproteins from parainfluenza viruses for use as a pharmaceutical substance as an active ingredient in a vaccine against disease caused by infection with parainfluenza viruses. The invention also extends to a pharmaceutical vaccinal composition containing HN and F glycoproteins from parainfluenza virus and optionally, a pharmaceutically acceptable carrier and/or diluent.

In a further aspect the invention provides the use of HN and F glycoproteins from parainfluenza viruses for the preparation of a pharmaceutical vaccinal composition for immunization against disease caused by infection with parainfluenza viruses.

1. Vaccine Preparation and Use

Immunogenic compositions, suitable to be used as vaccines, may be prepared from immunogenic HN and F glycoproteins of PIV-1, PIV-2 and/or PIV-3 as disclosed herein. Preferably, the antigenic material is extensively dialyzed to remove undesired small molecular weight molecules and/or lyophilized for more ready formulation into a desired vehicle. The immunogenic composition elicits an immune response which produces antibodies, including anti-PIV antibodies including anti-F and anti-HN antibodies. Such antibodies may be viral neutralizing.

Immunogenic compositions including vaccines may be prepared as injectables, as liquid solutions, suspensions or emulsions. The active immunogenic ingredient or ingredients may be mixed with pharmaceutically acceptable excipients which are compatible therewith. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Such suppositore may be formed from mixtures containing the active ingredient(s) in the range of about 0.5 to about 10%, preferably about 1 to 2%. Oral formulations may include normally employed incipients such as, pharmaceutical grades of saccharine, cellulose and magnesium carbonate. These compositions can take the form of solutions, suspensions, tablets, pills, capsules, sustained release formulations or powders and contain about 1 to 95% of the active ingredient(s), preferably about 20 to about 75%.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, the degree of protection desired, and if needed, to produce a cell-mediated immune response. Precise amounts of active ingredient required to be administered depend on the judgment of the practitioner. However, suitable dosage ranges are readily determinable by one skilled in the art and may be of the order of micrograms of the active ingredient(s) per vaccination. Suitable regimes for initial administration and booster doses are also variable, but may include an initial administration followed by subsequent administrations. The dosage may also depend on the route of administration and will vary according to the size of the host.

The concentration of the active ingredient protein in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen; or from combinations of various pathogens. In the present invention, as noted above, HN and F glycoproteins of PIV-1, PIV-2 and PIV-3 are combined in a single multivalent immunogenic composition which also may contain other immunogens.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum. The effectiveness of alum to enhance the immunogenicity of HN and F glycoproteins has been shown by Ewashyshyn et al. (ref. 16). While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T^H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283 and ref. 32) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Also, Nixon-George et al. (ref. 33), reported that octadecyl esters of aromatic amino acids complexed with a recombinant hepatitis B surface antigen, enhanced the host immune responses against hepatitis B virus.

2. Immunoassays

The HN and F glycoproteins of the present invention are useful as immunogens for the generation of antibodies thereto, as antigens in immunoassays including enzyme-linked immunosorbent assays (ELISA), RIAs and other non-enzyme linked antibody binding assays or procedures known in the art for the detection of antibodies. In ELISA assays, the selected HN or F glycoprotein or a mixture of glycoproteins is immobilized onto a selected surface, for example, a surface capable of binding proteins such as the wells of a polystyrene microtiter plate. After washing to remove incompletely adsorbed material, a nonspecific protein, such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from about 2 to 4 hours, at temperatures, such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound glycoprotein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a spectrophotometer.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, virology and immunology used but not explicitly described in this disclosure and these Examples are amply reported in the scientific literature and are well within the ability of those skilled in the art.

EXAMPLES

Example 1

This Example illustrates the production of high titres of PIV-1 on a mammalian cell line on microcarrier beads in large, controlled fermentors.

Vaccine quality African Green Monkey kidney cells (VERO cells) at a concentration of $10^5$ cells/mL were added to 60 to 75 L of CMRL 1969 media, pH 7.2, in a 150 L bioreactor containing 360 g of Cytodex-1 microcarrier beads and stirred for 2 hours. Additional CMRL 1969 was added to give a total volume of 150 L. Fetal bovine serum (FBS) was added to a final concentration of 3.5%. Glucose was added to a final concentration of 3.0 g/L and glutamine was added to a final concentration of 0.6 g/L. Dissolved oxygen (40%), pH (7.2), agitation (40 rpm) and temperature (37° C.) were controlled. Cell growth, glucose, lactate and glutamine levels were monitored. When cells were in logarithmic phases usually on days 3 to 4 reached a density of about $1.0-2.5 \times 10^6$ cells/mL. The culture medium was drained from the fermentor and 120 L of CMRL 1969, pH 7.2 (no FBS) was added and the culture stirred for 10 minutes. The draining and filling of the fermentor was usually repeated once but could be repeated up to three times. After washing the cells, the fermentor was drained and 50 L of CMRL 1969 containing 0.1% (v/v) FBS was added. The PIV-1 inoculum was added at a multiplicity of infection (m.o.i.) of 0.001. Trypsin was also added to promote efficient infection by proteolytic cleavage of the F protein if required. Additional CMRL 1969 with 0.1% FBS was added to give a final volume of 150 L. Incubation was continued at 34° C. for 4 to 6 days. One viral harvest was obtained from a single fermentor lot typically at 4 days post-infection. Multiple harvest from a single fermentation may also be obtained. Fluid was harvested according to the following procedure. The stirring was stopped and the beads were allowed to settle. The viral culture fluids were drained into a tank for further processing (See Example 4 below). PIV-1 growth was monitored by measurement of virus titres by tissue culture infectious dose ($TCID_{50}$), Haemagglutination (HA), HN and F antigen ELISA assays and results are shown in Table 1.

Example 2

This Example illustrates the production of high titres of PIV-2 on a mammalian cell line on microcarrier beads in large, controlled fermentors.

Vaccine quality African Green Monkey kidney cells (VERO cells) at a concentration of $10^5$ cells/ml were added to 60 L of CMRL 1969 media, pH 7.2 in a 150 L bioreactor containing 360 g of Cytodex-1 microcarrier beads and stirred for 2 hours. An additional 60 L of CMRL 1969 was added to give a total volume of 120 L. Foetal bovine serum (FBS) was added to achieve a final concentration of 3.5%. Glucose was added to a final concentration of 3.0 g/L and glutamine was added to a final concentration of 0.6 g/L. Dissolved oxygen (40%), pH (7.2), agitation (36 rpm) and temperature (37° C.) were controlled. Cell growth, glucose, lactate and glutamine levels were monitored. When cells were in logarithmic phase (usually on days 3–4) the cells had reached a density of about $1.0-2.5 \times 10^6$ cells/mL. The culture medium was drained from the fermentor and 60 L of CMRL 1969, pH 7.2 (no FBS) was added and stirred for 10 minutes. The draining and filling of the fermentor was usually repeated once but could be repeated up to three times. After washing the cells, the fermentor was drained and 120 L of CMRL 1969 containing 0.1% (v/v) FBS added. The PIV-2 inoculum was added at a multiplicity of infection (m.o.i.) of 0.001. Trypsin was also added to promote efficient infection by proteolytic cleavage of the F protein if required. Incubation was continued at 32°–37° C. for 3 to 6 days. One viral harvest was from a single fermentor lot typically 4 days post-infection. Multiple harvests from a single fermentation may also be obtained. The fluid was harvested according to the following procedure. The stirring was stopped and the beads were allowed to settle. The viral culture fluids were drained into a tank for further processing (See Example 4 below). PIV-2 growth was monitored by measurement of virus titres by $TCID_{50}$, Haemagglutination (HA), whole virus and F antigen ELISA assays and the results are shown in Table 2.

Example 3

This Example illustrates the production of high infectious titres of PIV-3 on a mammalian cell line on microcarrier beads in large, controlled fermentors.

Vaccine quality African Green Monkey kidney cells (VERO cells) at a concentration of $10^5$ cells/ml were added to 60 L of CMRL 1969 media, pH 7.2 in a 150 L bioreactor containing 360 g of Cytodex-1 microcarrier beads and stirred for 2 hours. An additional 60 L of CMRL 1969 was added to give a total volume of 120 L. Fetal bovine serum (FBS) was added to achieve a final concentration of 7.0%. Glucose was added to a final concentration of 3.0 g/L and glutamine was added to a final concentration of 0.6 g/L. Dissolved oxygen (40%), pH (7.2), agitation (36 rpm) and temperature (37° C.) were controlled. Cell growth, glucose, lactate and glutamine levels were monitored. At day 4 the cells had achieved concentrations of about $1.0-1.8 \times 10^6$ cells/mL. The culture medium was drained from the fermentor and 100 L of CMRL 1969, pH 7.2 (no FBS) was added and stirred for 10 minutes. The draining and filling of the fermentor was usually repeated once but could be repeated up to three times. After washing the cells, the fermentor was drained a third time and 60 L of CMRL 1969 added. The PIV-3 inoculum was added at a multiplicity of infection (m.o.i.) of 0.001 and the culture and stirred for 2 hours at 37° C. An additional 60 L of CMRL 1969, pH 7.2 was added and incubation continued under the same conditions. Multiple viral harvests can be obtained from a single fermentor lot typically on days 4, 7, 10 post-infection. Viral fluid was harvested according to the following procedure. The stirring was stopped and the beads were allowed to settle. The viral culture fluids were drained into a tank for further processing (See Example 4). The fermentor was filled again with 120 L CMRL 1969 medium and incubated as described above. PIV-3 growth was monitored by measurement of virus titres by $TCID_{50}$, Haemagglutination (HA) a virus antigen ELISA assays and the results are shown in Table 3. The yield of viral protein was 8–12 mg/L.

PIV could also be produced on vaccine quality human lung diploid cells (MRC-5) using a similar procedure.

Example 4

This Example describes the clarification and concentration of the PIV viral harvests.

For PIV-1, the viral harvest (150 L) was filtered through a series of dead-end filters (1.2 μm followed by a 0.45 μm). The clarified harvest fluid was concentrated 40 to 150 fold using tangential flow ultrafiltration with 300 NMWL membranes and diafiltered with PBS. Virus recovery throughout the processing was measured by HA, $TCID_{50}$ and ELISA. Viral harvests could be stored frozen (−20° C. or −70° C.) prior to further purification as described below in Examples 3–6.

For PIV-2, the viral harvest (120 L) was filtered through a 1 μm dead-end filter. The clarified harvest fluid was concentrated 40–90 fold using tangential flow ultrafiltration with 300 NMWL membranes and diafiltered with PBS. Virus recovery throughout the processing was measured by HA, and was high greater than 75%. Viral harvests could be stored frozen (−20° C. or −70° C.) in the presence of protease inhibitors—such as 1 mM Pefabloc, prior to further purification.

For PIV-3, the viral harvest (120 L) was filtered through a series of dead-end filters (20 μm −>1 μm −>0.45 μm, Sartorius) or alternatively processed by 0.45 μm tangential flow microfiltration. The clarified harvest fluids were concentrated 40–50 fold using tangential flow ultrafiltration with 300 NMWL membranes and diafiltered with PBS. Virus recovery throughout the processing was measured by HA, $TCID_{50}$ and ELISA assays and was typically greater than 80%. Viral harvests could be stored frozen (−20 C. or −70° C.) until purified further.

Example 5

This Example describes the purification of PIV-1 hemagglutinin-neuraminidase (HN) and Fusion (F) glycoproteins.

The virus harvest concentrate was centrifuged at 28,000× g for 30 minutes at 4° C. The supernatant was discarded and the pellet resuspended in extraction buffer consisting of 10 mM Tris-HCl, pH 7.0, 150 mM NaCl, 2% (w/v) Triton X-100 to the original harvest concentrate volume. Pefabloc was added to a final concentration of 5 mM. The suspension was stirred at room temperature for 30 minutes. The supernatant, containing the soluble HN and F glycoproteins, was clarified by centrifugation at 28,000× g for 30 minutes at 4° C.

A TMAE—Fractogel column (10 cm×15 cm) was equilibrated with 10 mM Tris-HCl, pH 7.0, 150 mM NaCl containing 0.02% Triton X-100. The Triton X-100 supernatant (−1 mg extract loaded/mL resin), containing the soluble HN & F proteins, was loaded directly onto the TRAE-Fractogel column. The total volume added plus 2 bed volumes of 10 mM Tris-HCl, pH 7.0, 150 mM NaCl containing 0.02% Triton X-100 were collected. The TMAE—Fractogel flow-through containing the HN and F was diluted 3-fold with 10 mM Tris-HCl, pH 7.0, containing 0.02% Triton X-100.

An hydroxyapatite column (10 cm×15 cm) was equilibrated with 10 mM Tris-HCl, pH 7.0, 50 mM NaCl, 0.02% Triton X-100. After loading the TMAE flow-through, the column was washed with 2 column volumes of 10 mM Tris-HCl, pH 7.0, 50 mM NaCl , 0.02% Triton X-100 followed by 4 column volumes of 5 mM sodium phosphate, pH 7.0, 1M NaCl, 0.02% Triton X-100. The proteins were eluted with 4 column volumes of 20 mM sodium phosphate, pH 7.0, 1M NaCl , 0.02% Triton X-100. Fractions were collected based on $A_{280}$ and the protein content and antigen concentrations were measured.

The co-purified HN and F glycoproteins were ultrafiltered by tangential flow ultrafiltration using a 300 kDa NMWL membrane. The 300 kDa filtrate was PEG precipitated by addition of PEG to a final concentration of 10% followed by stirring at 2 to 8° C. for 1 hour. The suspension was then centrifuged at 28,000× g for 1 hour at 4° C. The pellet was resuspended in PBS to a protein concentration of 200–300 pg/mL. The sample was stirred for 1 hour at 20° C. to 25° C. and dialyzed (6,000 to 8,000 molecular weight cut-off) for three days at 4° C. against PBS containing 0.02% Triton X-100.

The dialyzed HN and F glycoproteins were sterile-filtered on a dead end 0.2 to 0.22 μm membrane filter and adsorbed onto aluminum phosphate (0.75–3 mg/mL final concentration).

Example 6

This Example describes the purification of PIV-2 Hemagglutinin-Neuraminidase (HN) and Fusion (F).

The virus harvest concentrate was PEG precipitated by addition of 50% PEG to a final concentration of 4% and the mixture incubated at 2–8° C. for 1 hour. The suspension was then centrifuged at 28,000× g for 30 minutes at 4° C. and the pellet resuspended in 2M urea in PBS to half the original volume. The suspension was stirred for 1 hour at 20–25° C. and then centrifuged at 28,000× g for 1 hour at 4° C. The pellet was resuspended in 10 mM Tris-HCl, pH 8.5, 150 mM NaCl buffer to 1/10 the original volume. The sample was then frozen at −20° C. or processed immediately.

Triton X-100 (10%) was added to the urea-washed virus suspension to a final concentration of 2% and stirred at 20–25° C. for 2 hours. The supernatant containing the soluble HN & F glycoproteins, was clarified by centrifugation at 28,000× g for 30 minutes at 4° C.

A TMAE—Fractogel column (1.5 cm×30 cm) was equilibrated with 10 mM Tris-HCl, pH 8.5, 50 mM NaCl containing 0.01% Triton X-100. The Triton X-100 supernatant (−1 mg extract loaded/mL resin), containing the soluble HN & F proteins, was diluted 2-fold with 10 mM Tris-HCl, pH 8.5 and loaded directly onto the TMAE—Fractogel column. The total volume added plus 2 bed volumes of 10 mM Tris-HCl, pH 8.5, 50 mM NaCl containing 0.01% Triton X-100 were collected. The TMAE—Fractogel flow through contains the soluble F glycoprotein. The TMAE column is washed with 4 column volumes of 10 mM Tris-HCl, pH 8.5, 200 mM NaCl, 0.01% Triton X-100. The HN glycoproteins were eluted with 10 mM Tris-HCl, pH 8.5, 300 mM NaCl, 0.01% Triton X-100.

Benzonase was added to the HN-enriched fraction from the TMAE-Fractogel column and the mixture made 1 mM with $MgCl_2$. This mixture was incubated overnight at room temperature.

An hydroxyapatite column (2.5 cm×10 cm) was equilibrated with 10 mM Tris-HCl, pH 8.5 containing 50 mM NaCl and 0.01% Triton X-100. The TMAE flow-through was loaded onto the hydroxypatite column and the $UV_{280}$ absorbing flow-through (containing the F-glycoprotein) plus 2 column volumes of 10 mM Tris-HCl, pH 8.5 containing 50 mM NaCl and 0.01% Triton X-100 were collected.

The hydroxyapatite flow-through was made 30 mM with sodium acetate and loaded onto a $SO_3$-Fractogel column pre-equilibrated with 10 mM sodium acetate, pH 5.0, 50 mM NaCl, 0.01% Triton X-100. The column was washed with 2 column volumes of 10 mM sodium acetate, pH 5.0, 50 mM NaCl, 0.01% Triton X-100. The column was further washed with 2 column volumes of 10 mM sodium acetate, pH 5.0, 0.2M NaCl, 0.01% Triton X-100. The F glycoprotein was eluted with 4 column volumes of 10 mM sodium acetate, pH 5.0, 1M NaCl, 0.01% Triton X-100 and the $A_{280}$ absorbing peak plus 2 column volumes of 10 mM Tris-HCl, pH 5.0, 1M NaCl, 0.01% Triton X-100 were collected.

An S-300 column (1.5 cm×90 cm) was packed and equilibrated with 50 mM potassium phosphate, pH 7.5, 0.5M NaCl, 0.01% Triton X-100. The TMAE eluate containing the soluble HN-glycoprotein was concentrated in a stirred cell concentrator at 4° C. to give a final volume of approximately 2% of the S-300 column volume and loaded onto the S-300 gel filtration column. The column was eluted with 50 mM potassium phosphate, pH 7.5, 0.5M NaCl, 0.01% Triton X-100, 10% glycerol and $A_{280}$ absorbing peaks (2–4 column volumes) containing HN-glycoprotein collected.

Alternatively, the TMAE eluate was diluted 5-fold with 10 mM Tris-HCl, pH 8.5, 0.01% Triton X-100 and loaded onto an hydroxyapatite column (5 cm×15 cm) equilibrated with 10 mM Tris-HCl, pH 8.5, 50 mM NaCl, 0.01% Triton X-100. The column was washed with 4 column volumes of 50 mM sodium phosphate, pH 8.5, 0.01% Triton X-100. The HN-glycoprotein was eluted with 4 column volumes of 100 mM sodium phosphate, pH 8.5, 0.15M NaCl, 0.01% Triton X-100. The purified HN and F glycoproteins were ultrafiltered by tangential flow ultrafiltration using a 300 kDa NMWL membrane. The 300 kDa filtrate was concentrated and by tangential flow ultrafiltration using a 20 kDa NMWL membrane to a protein concentration of 200–300 µg/mL followed by diafiltration against PBS containing 0.01% Triton X-100.

The concentrated HN and F glycoproteins were sterile-filtered on a dead end 0.2–0.22 um membrane filter and adsorbed onto aluminum phosphate (0.75–3 mg/mL final concentration).

Example 7

This Example describes the purification of PIV-3 Hemagglutinin-Neuraminidase (HN) and Fusion (F) glycoproteins.

PIV-3 could be separately purified from each viral harvest or the viral harvests were pooled. PIV-3 was precipitated from the viral harvests by addition of PEG 6000–8000 to a final concentration of about 2% (w/v) and stirring for about 2 hours at 4° C. The precipitate was collected by centrifugation and the pellet resuspended in phosphate buffered saline. TRITON X-100 was added to achieve a final concentration of 1% (v/v) and the mixture stirred for 1–3 hours at 37° C. to extract the HN and F glycoproteins. Unsolubilized protein was removed by centrifugation. Most of the HN and F glycoproteins were found in the supernatant.

Alternatively, a Sephacryl S-500 column (2.5×100 cm) was equilibrated with 50 mM phosphate buffer, pH 7.5 containing 0.25M NaCl at a flow rate of 2.5 ml/min. The viral retentate pool (100 ml) was loaded on to the column and the column effluent was monitored at $A_{280}$. PIV-3 eluted in the void volume. Fractions were also analysed for HA activity and by SDS-PAGE. There was good separation of virus from protein contaminants with high recovery of HA activity (>80%). The fractions containing PIV-3 were pooled and subjected to detergent extraction as described above.

Alternatively, cellufine sulphate can be used for purification of PIV-3 directly if the number of washes of the cells prior to infection is increased from two to four. A cellufine sulfate column (10 cm×15 cm) was equilibrated with 10 mM Tris.HCl, pH 7.3, 0.15M NaCl. The viral harvest concentrate (2.5 mg loaded/ml cellufine sulfate) was loaded on the column at a flow rate of 2 mL/min. After loading, the column was washed with five column volumes of the equilibration buffer. Virus and viral fragments were eluted with 50 mM Tris.HCl, 1.5M NaCl containing 2% Triton X-100. The elution pool was then incubated for 2–3 hours at room temperature or 37° C. to extract the HN & F glycoproteins. Insoluble material was removed by centrifugation.

A cellufine sulfate column of an appropriate size (~1 mg extract loaded/ml resin) was equilibrated with 10 mM Tris.HCl, pH 7.5, 0.15M NaCl, 0.02% Triton X-100. The conductivity of the detergent extract or the TMAE-Fractogel elution pool was adjusted to approximately 4 mS/cm or less by addition of distilled water or 0.02% Triton X-100 and loaded onto the column at a linear flow rate of 50 cm/h. After loading, the column was washed with five column volumes of equilibration buffer. The HN and F glycoproteins were eluted with 10 mM Tris.HCl, pH 7.5 containing 1.0M NaCl, 0.02% Triton X-100. Fractions were collected and the absorbance was monitored at $A_{280}$. The peak was pooled and assayed for protein content and HA activity. HN & F proteins were recovered in the elution fraction from the cellufine sulfate column.

The HN and F enriched extract (virus purified by gel filtration chromatography) or the HN and F pool from cellufine sulfate were further purified by anion exchange chromatography.

A TMAE-Fractogel column (~2.5 mg extract or cellufine sulfate elution pool loaded/mL resin) was equilibrated with 10 mM Tris.HCl, pH 7.5 containing 0.05M NaCl, 0.02% Triton X-100. The conductivity of the extract or cellufine sulfate elution pool was adjusted to a conductivity of less than or equal to 4 mS/cm with distilled water and the sample loaded on the column at a linear flow rate of 100 cm/h. After loading the sample, the column was washed with 5 column volumes of the equilibration buffer followed by 5 column volumes of 10 mM Tris.HCl, pH 7.5, 0.15M NaCl, 0.02% Triton X-100. The proteins were eluted with 10 mM Tris.HCl, pH 7.5, 0.6M NaCl, 0.02% Triton X-100. Fractions were collected and pooled based on $A_{280}$ values and the protein content and HA activity of the fractions were measured.

The co-purified HN and F glycoproteins were ultrafiltered by tangential flow ultrafiltration using a 300 kDa NMWL membrane and diafiltered with PBS. The 300 kDa filtrate and diafiltrate containing the HN and F proteins were combined and re-concentrated using 30 kDa membranes and diafiltered with PBS. The concentrated glycoprotein preparation was 0.22 µm sterile-filtered and adsorbed onto aluminum phosphate (0.75 to 3 mg/mL final concentration).

Example 8

This Example illustrates the analysis of the PIV HN and F glycoprotein preparations by SDS-PAGE, immunobloting and scanning Densitometry.

Figure 2A:
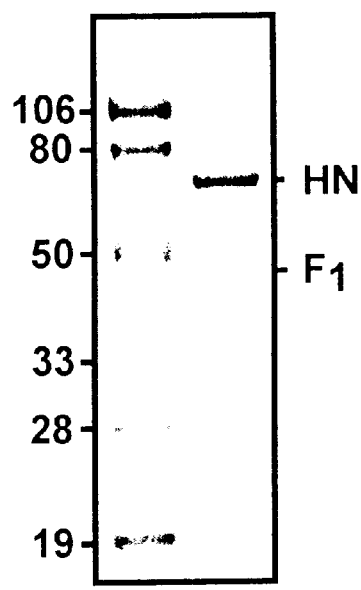
FIG. 2(a) is an analysis of purified parainfluenza virus type 1 HN and F glycoproteins by sodium dodecyl sulphate polyacrylamide gel electrophoresis.
Figure 2B:
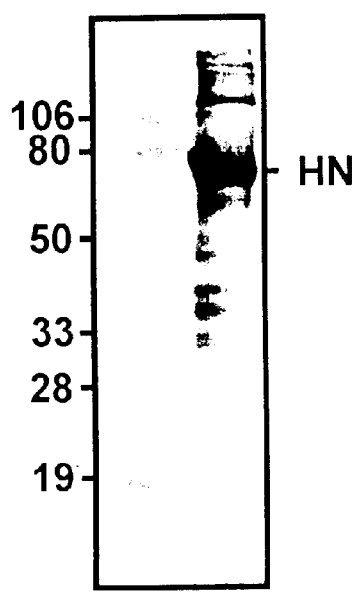
FIG. 2(b) is an analysis of purified parainfluenza virus type 1 HN glycoprotein by immunoblot analysis and detection is with an anti-PIV-1 HN antibody.
Figure 2C:
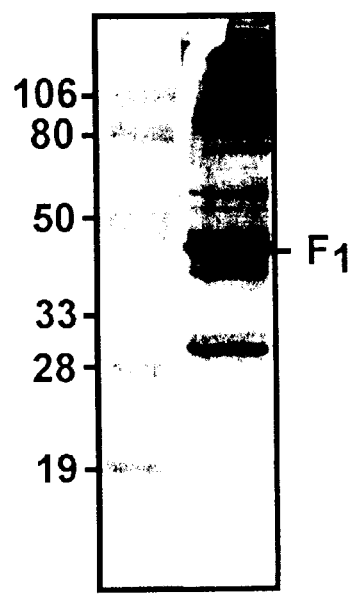
FIG. 2(c) is an analysis of purified parainfluenza virus type 1 F glycoprotein by immunoblot analysis and. detection is with an anti-PIV-1 F antibody.
Figure 3A:
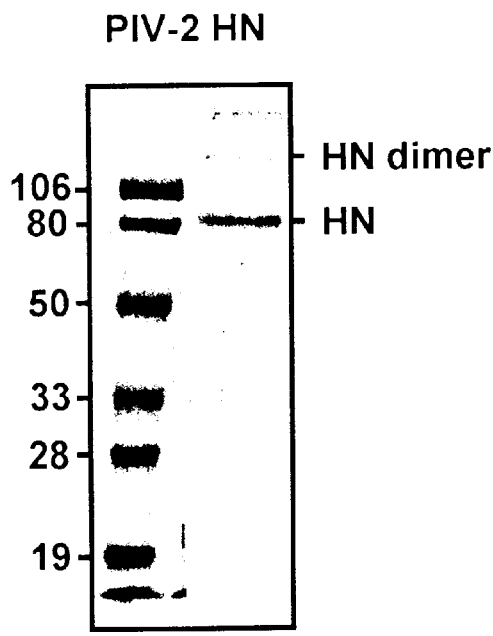
FIG. 3(a) is an analysis of purified parainfluenza. virus type 2 HN glycoprotein by sodium dodecyl sulphate polyacrylamide gel electrophoresis.
Figure 3C:
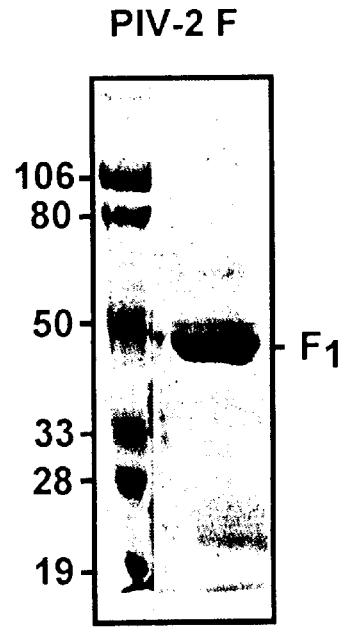
FIG. 3(c) is an analysis of purified parainfluenza virus type 2 F protein by sodium dodecyl sulphate polyacrylamide gel electrophoresis.
Figure 3B:
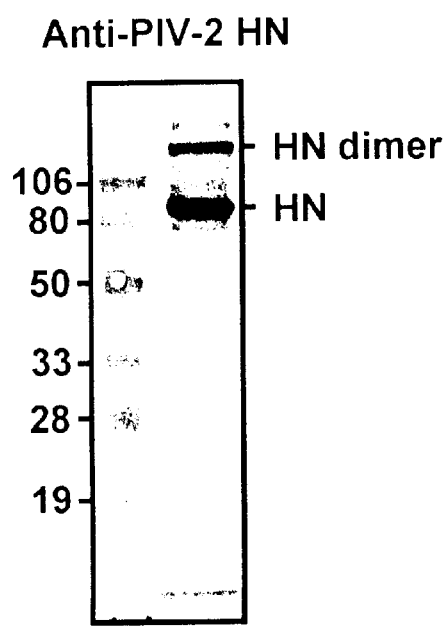
FIG. 3(b) is an analysis of purified parainfluenza. virus type 2 HN glycoprotein by immunoblot analysis and detection is with an anti PIV-2 HN antibody.
Figure 3D:
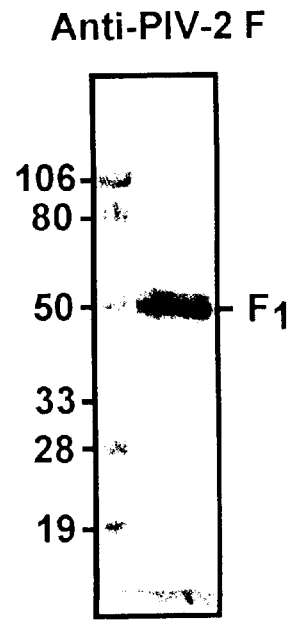
FIG. 3(d) is an analysis of purified parainfluenza virus type 2 F glycoprotein by immunoblot analysis and detection is with an anti-PIV-2 F antibody.
Figures 4A, 4B:
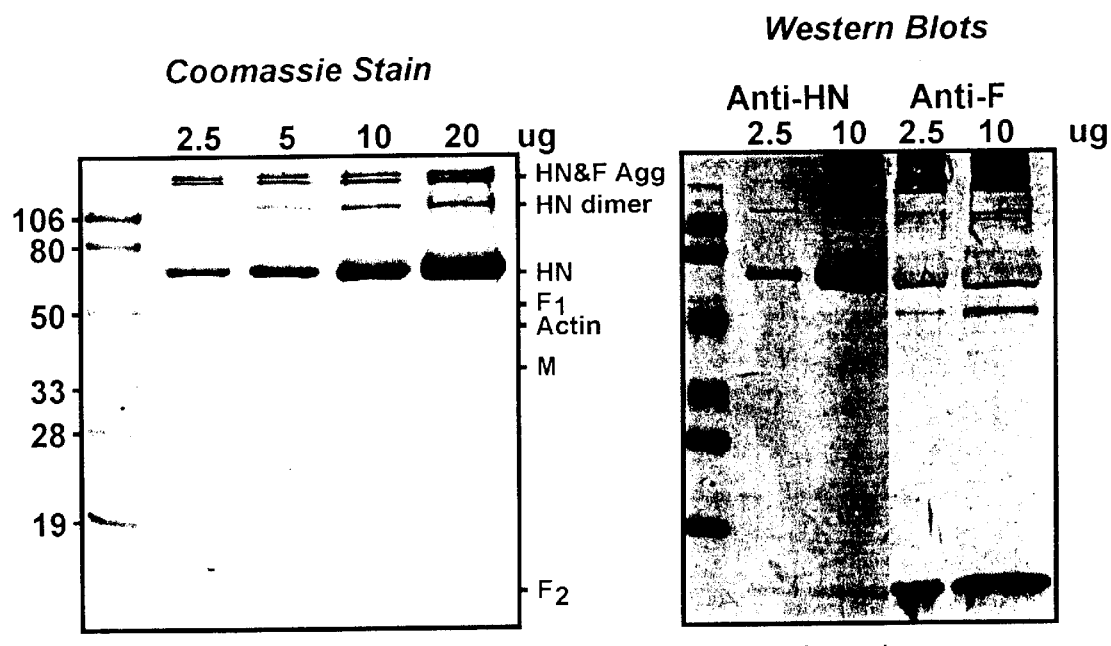
FIG. 4(a) is an analysis of purified parainfluenza virus type 3 HN and F glycoproteins by sodium dodecyl sulphate polyacrylamide gel electrophoresis under reducing conditions.
FIG. 4(b) is an analysis of purified parainfluenza virus type 3 HN and F glycoproteins by immunoblot detection of proteins separated by SDS-polyacrylamide gel. electrophoresis under reducing conditions using HN and F specific antibodies.
Figures 4C, 4D:
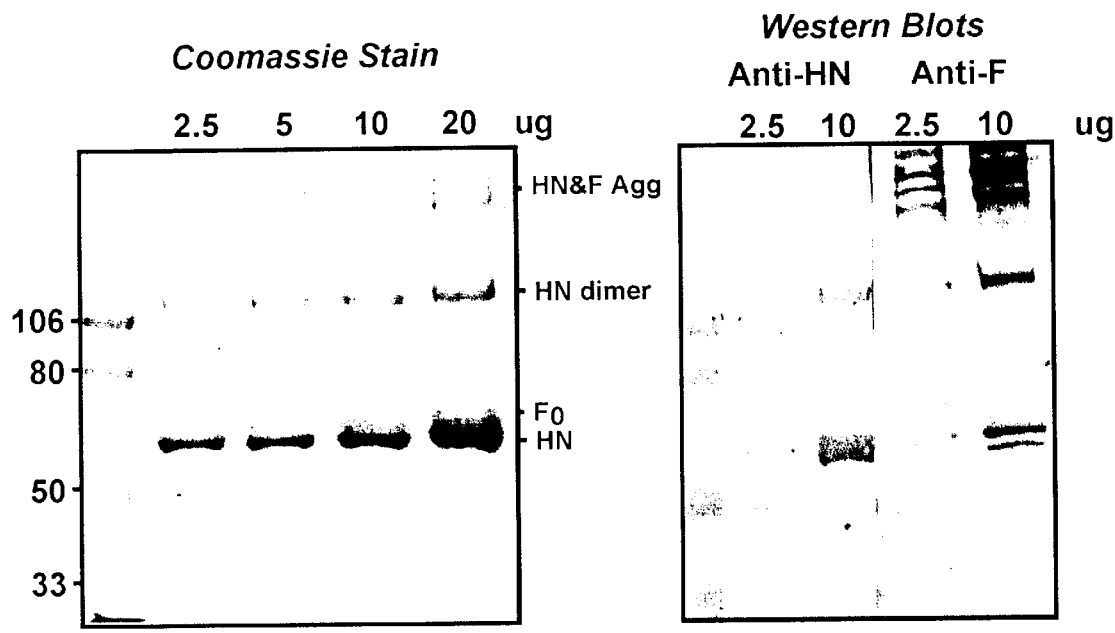
FIG. 4(c) is an analysis of purified parainfluenza virus type 3 HN and F glycoprotein by sodium dodecyl sulphate polyacrylamide gel electrophoresis under non-reducing conditions.
FIG. 4(d) is an analysis of purified parainfluenza virus type 3 HN and F glycoprotein by immunoblot detection of proteins separated by SDS-polyacrylamide gel electrophoresis under non-reducing conditions using HN and F specific antibodies.

The PIV HN and F glycoprotein preparations were run on 12.5% SDS-PAGE gels under reducing conditions or on 7.5% SDS-PAGE gels under non-reducing conditions. Gels were stained with Coomassie Blue. Higher molecular weight forms of both the HN and F proteins were detected. Immunoblot analysis was used to confirm the identity of the higher molecular weight forms using mono-specific anti-HN and anti-F antisera or monoclonal antibodies. The total amount of HN and F proteins present in the preparations was determined by scanning each lane using a laser densitometer and totalling the area under the peaks corresponding to the HN and F protein bands. The results from these analyses are shown in FIGS. 2(a) to 2(c) for PIV-1, FIGS. 3(a) to 3(d) for PIV-2 and 4(a) to 4(d) for PIV-3.

Example 9

This Example illustrates the immunogenicity of PIV-1 HN and F glycoproteins in mice.

Figures 5A, 5B:
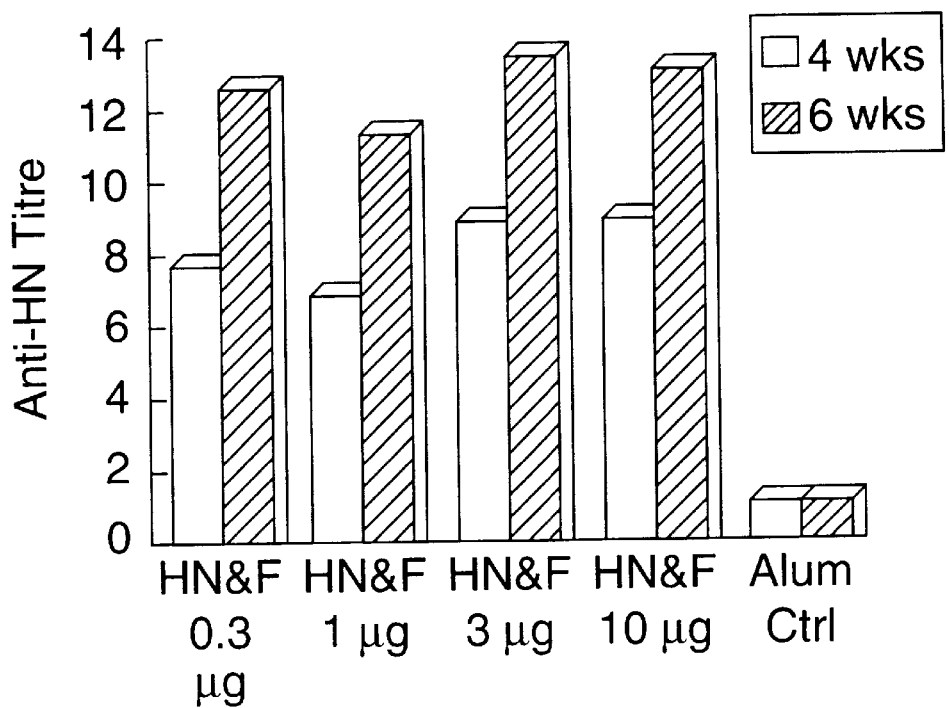
FIGS. 5(a) and 5(b) show the anti-HN antibody response in mice immunized with purified parainfluenza virus type 1 HN and F glycoproteins.
Figures 5C, 5D:
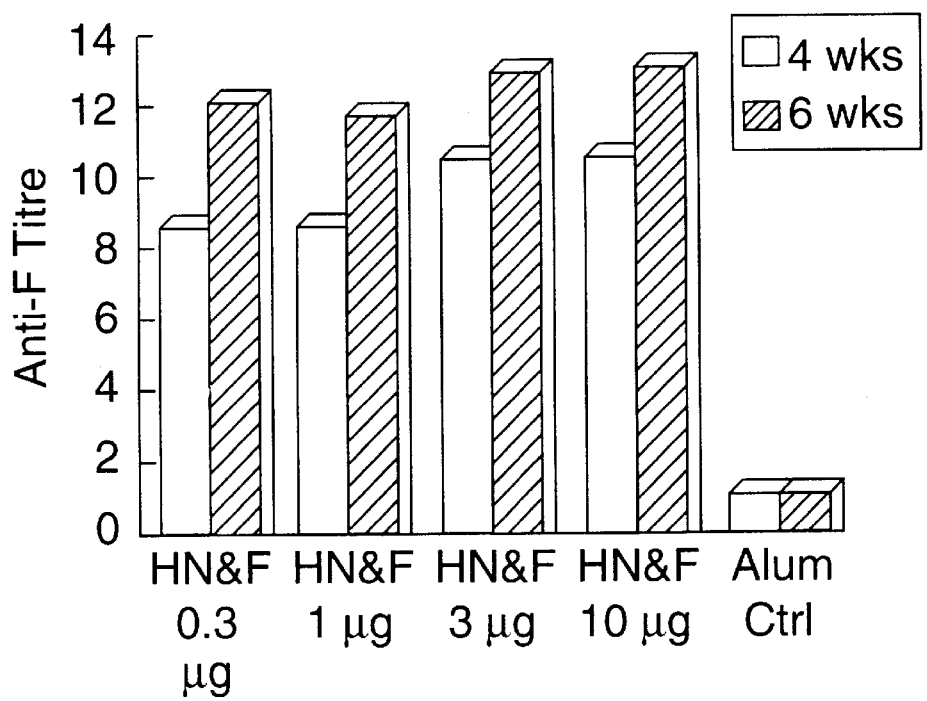
FIGS. 5(c) and 5(d) show the anti-F antibody response in mice immunized with purified parainfluenza virus type 1 HN and F glycoproteins.
Figures 5E, 5F:
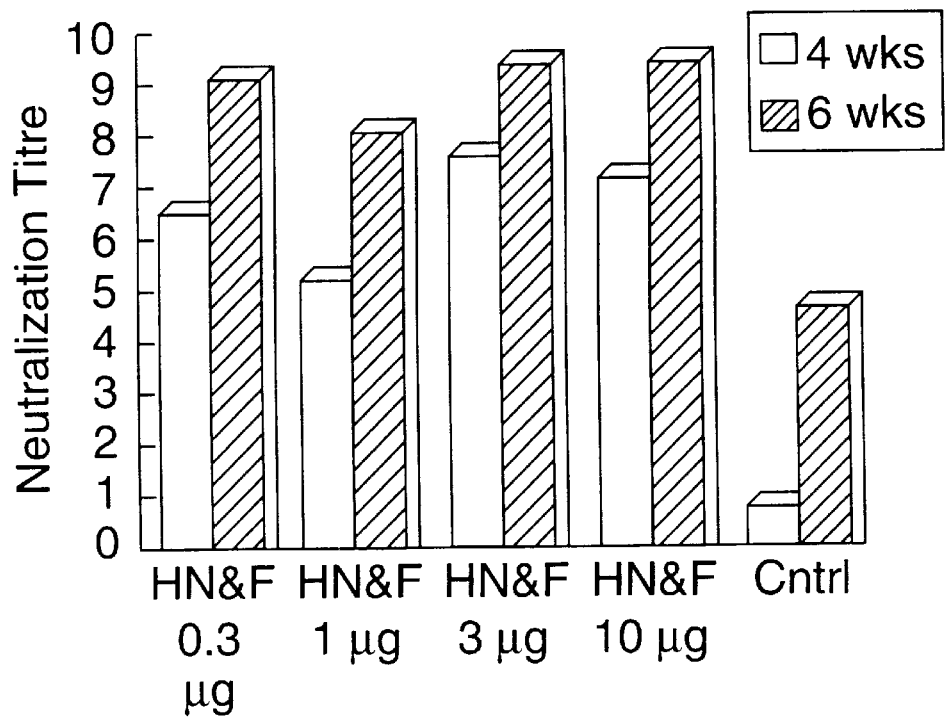
FIGS. 5(e) and 5(f) show the PIV-1 neutralization tires of sera from mice immunized with purified parainfluenza virus type 1 HN and F glycoproteins.

Groups of 5 mice (CD-1, 18–20 g) were immunized intraperitoneally (0.5 mL) on day 0 and day 28 with 0.3, 1, 3, or 10 μg of PIV-1 HN&F glycoproteins adjuvanted with 3 mg/mL aluminum phosphate (alum). Blood samples were taken on days 0, 28 and 42. Mice immunized with PBS/alum served as negative controls. Sera were analyzed for anti-HN, anti-F antibody titres and PIV-1 specific neutralizing titres. Strong anti-HN, anti-F and neutralizing antibody responses were detected at 4 weeks and 6 weeks for all doses tested. Results are summarized in FIGS. 5(a) to 5(c).

Example 10

This Example illustrates the immunogenicity of PIV-1 HN and F glycoproteins in hamsters.

Figures 6A, 6B:
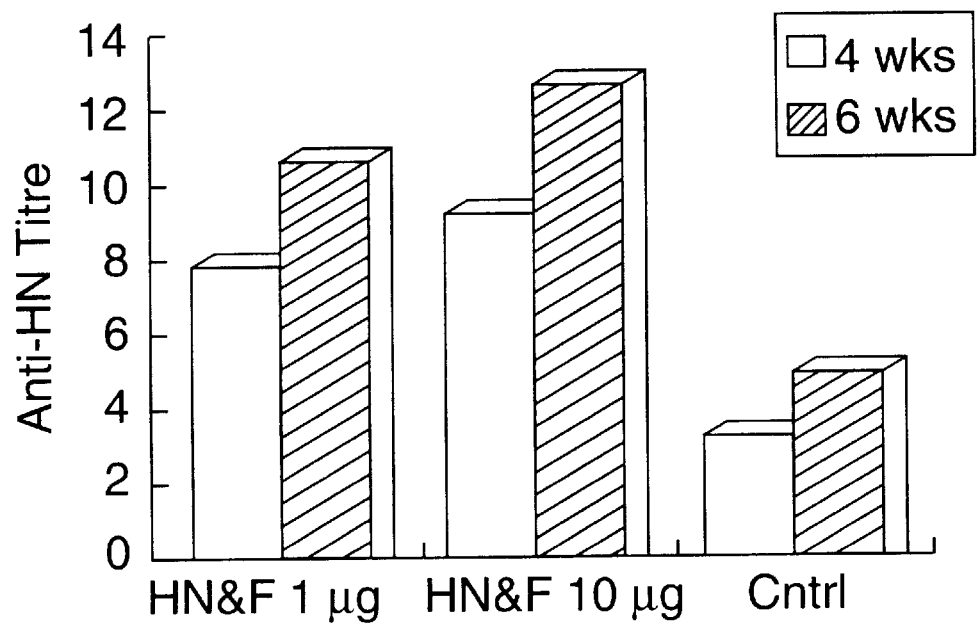
FIGS. 6(a) and 6(b) show the anti-HN antibody response in hamsters immunized with purified parainfluenza virus type 1 HN and F glycoproteins.
Figures 6C, 6D:
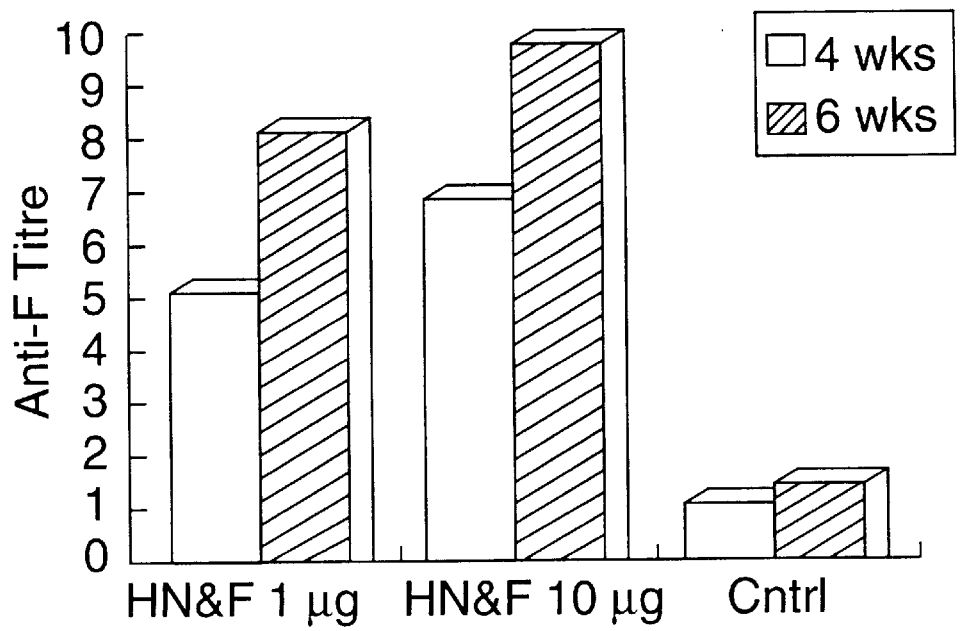
FIGS. 6(c) and 6(d) show the anti-F antibody response in hamsters immunized with purified parainfluenza virus type 1 HN and F glycoproteins.
Figures 6E, 6F:
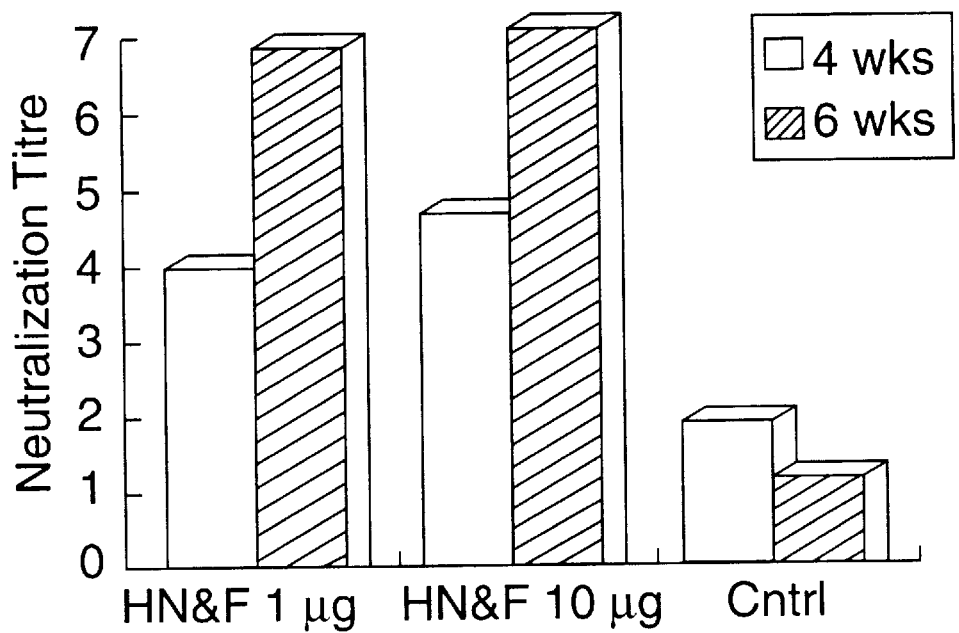
FIGS. 6(e) and 6(f) show the PIV-1 neutralization tires of sera from hamsters immunized with purified parainfluenza virus type 1 HN and F glycoproteins.

Groups of 10 hamsters (golden Syrian, Charles River) were immunized intramuscularly (0.5 mL) on day 0 and day 28 with 1 or 10 μg of PIV-1 HN&F glycoproteins adjuvanted with 3 mg/mL aluminum phosphate (alum). Blood samples were taken on days 0, 28 and 42. Hamsters immunized with PBS/alum served as negative controls. Sera were analyzed for anti-HN, anti-F titres and PIV-1 specific neutralizing titres. Strong anti-HN, anti-F and neutralizing antibody responses were seen at both 4 weeks and 6 weeks for all doses tested. Results are summarized in FIGS. 6(a) to 6(c).

Example 11

This Example illustrates the immunogenicity of PIV-2 HN and F glycoproteins in mice.

Figures 7A, 7B:
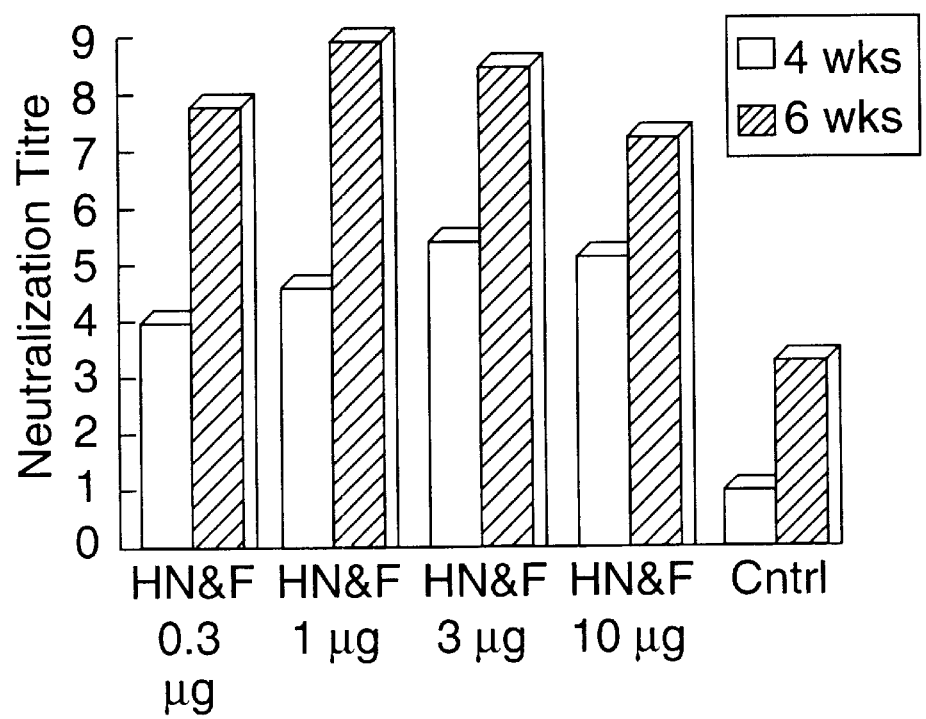
FIGS. 7(a) and 7(b) show the PIV-2 neutralization titres of sera from mice immunized with a mixture of separately purified parainfluenza type 2 HN and F glycoproteins combined in a ratio of about 1:1.

Groups of 5 mice (CD-1, 18–20 g) were immunized intraperitoneally (0.5 mL) on day 0 and day 28 with 0.3, 1, 3, or 10 μg of PIV-2 HN&F glycoproteins adjuvanted with 3 mg/mL aluminum phosphate (alum). Purified PIV-2 HN and F glycoproteins were mixed in a 1:1 ratio (eg. a 10 μg dose would contain 5 μg of HN and 5 μg of F). Blood samples were taken on days 0, 28 and 42. Mice immunized with PBS/alum served as negative controls. Sera were analyzed for anti-HN, anti-F titres and PIV-2 specific neutralizing titres. PIV-2 neutralizing antibody responses were detected at 4 and 6 weeks for all doses tested. Results are summarized in FIG. 7.

Example 12

This Example illustrates the immunogenicity of PIV-2 HN and F glycoproteins in mice with different HN:F ratios.

Figures 8A, 8B:
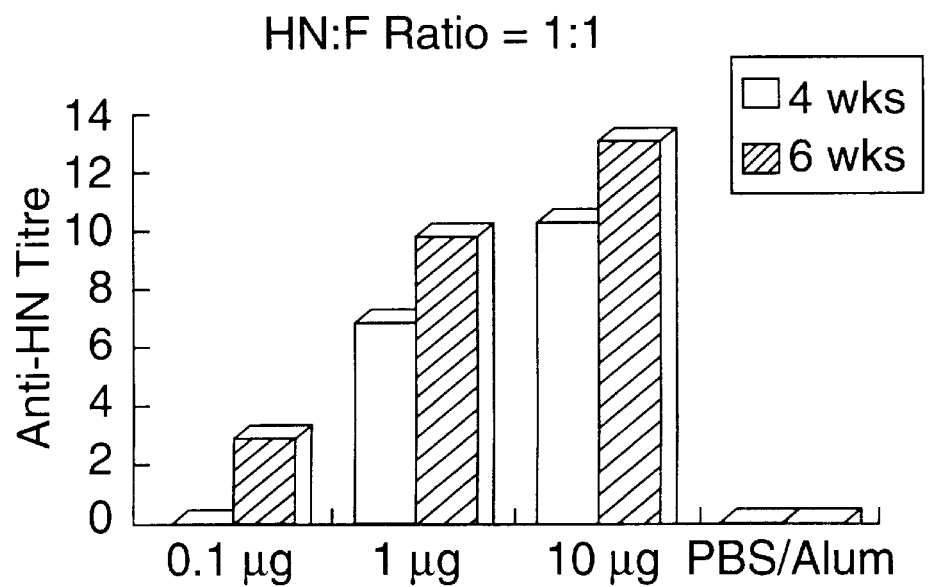
FIGS. 8(a)–8(d) show the anti-HN antibody response in mice immunized with a mixture of separately purified parainfluenza type 2 HN and F glycoproteins combined in a number of ratios.
Figure 8C:
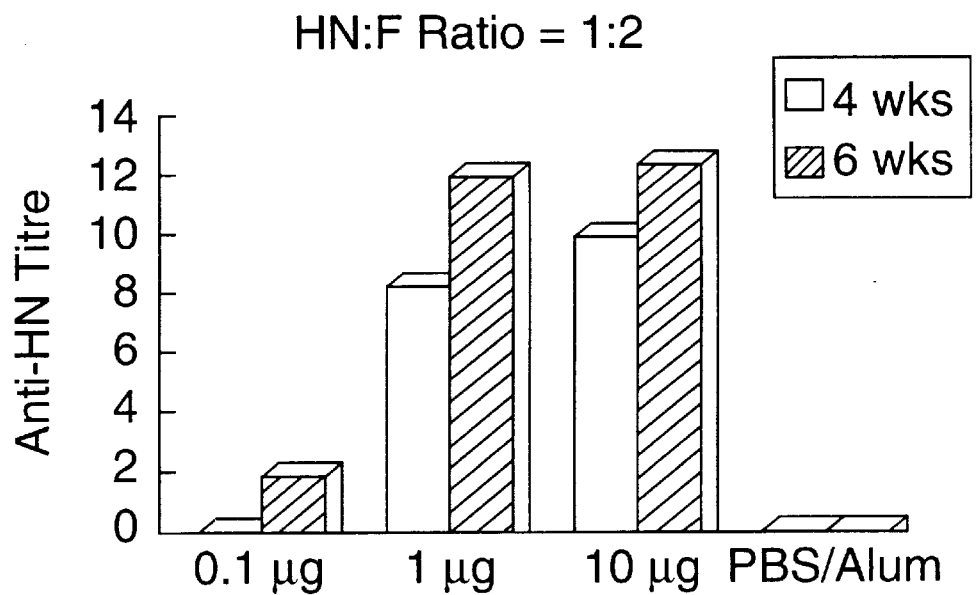
Figure 8D:
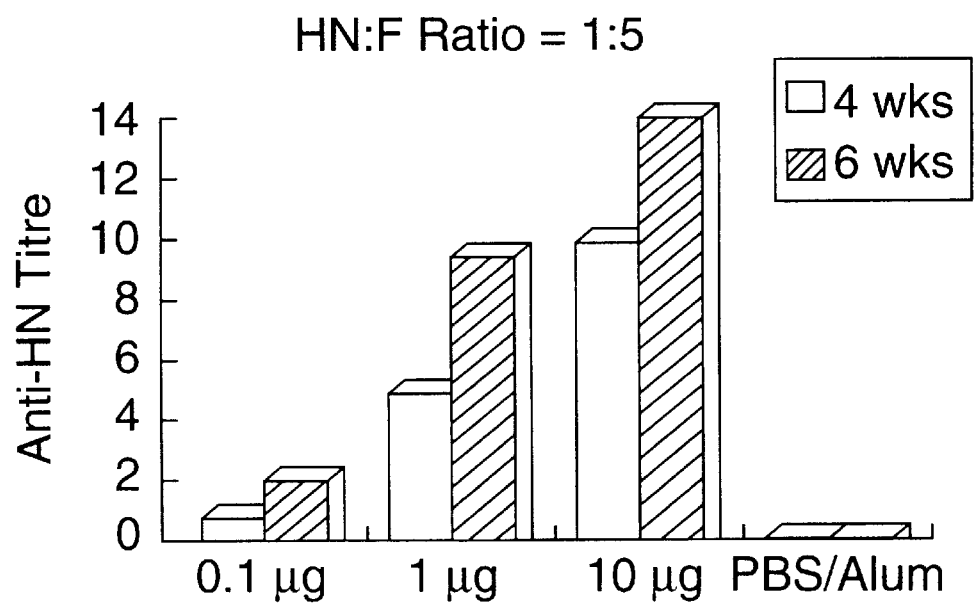
Figures 9A, 9B:
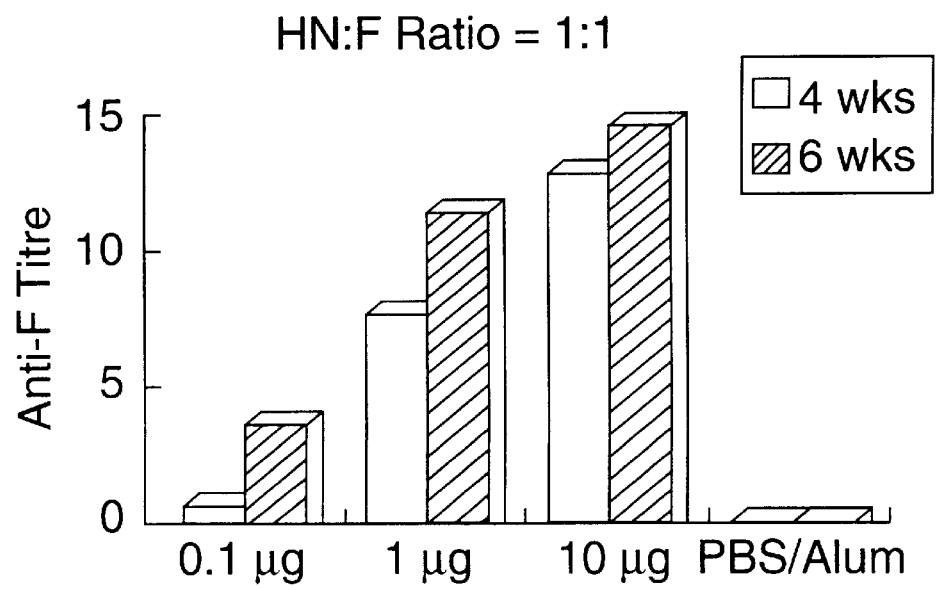
FIGS. 9(a)–9(d) show the anti-F antibody response in mice immunized with a mixture of separately purified parainfluenza type 2 HN and F glycoproteins combined in a number of ratios.
Figure 9C:
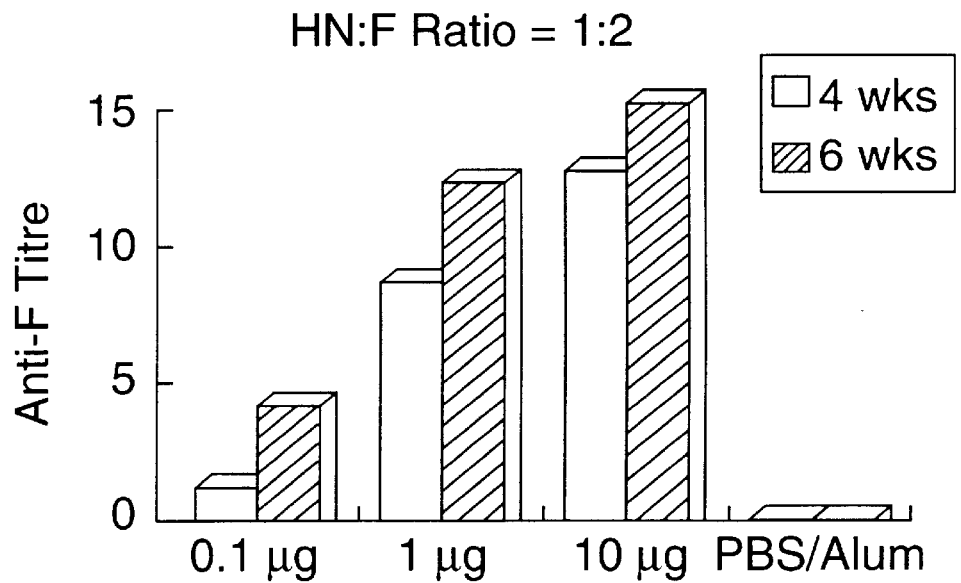
Figure 9D:
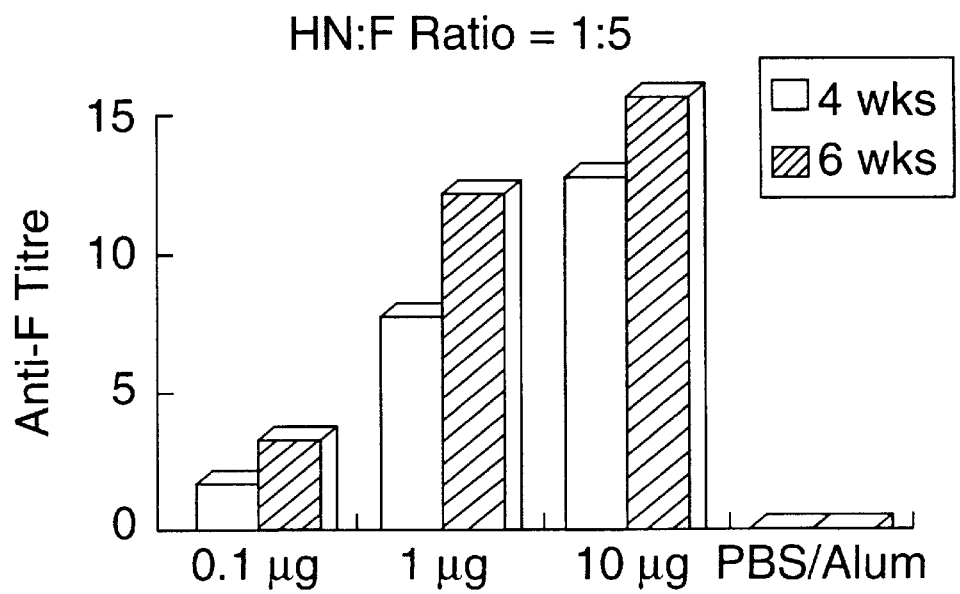
Figures 10A, 10B:
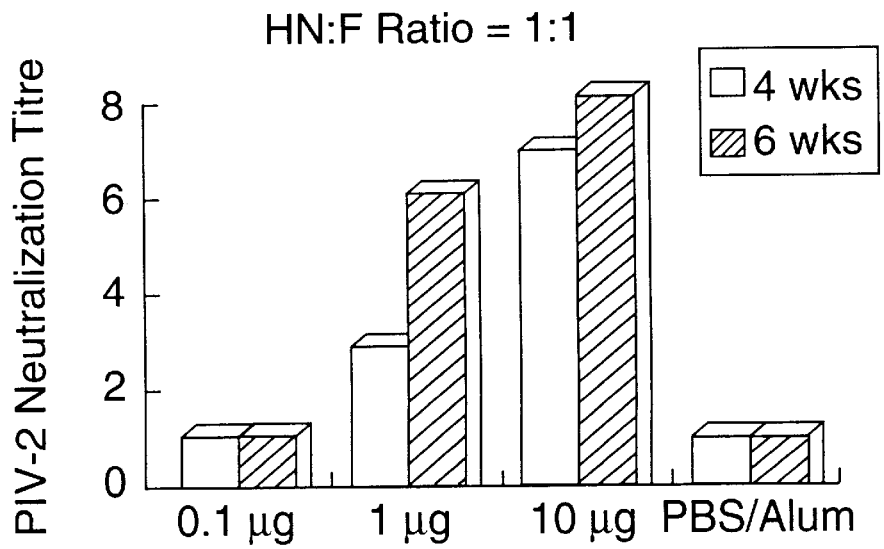
FIGS. 10(a)–10(d) show the PIV-2 neutralization tires of sera from mice immunized with a mixture of separately purified parainfluenza virus type 2 HN and F glycoproteins combined in a number of ratios.
Figure 10C:
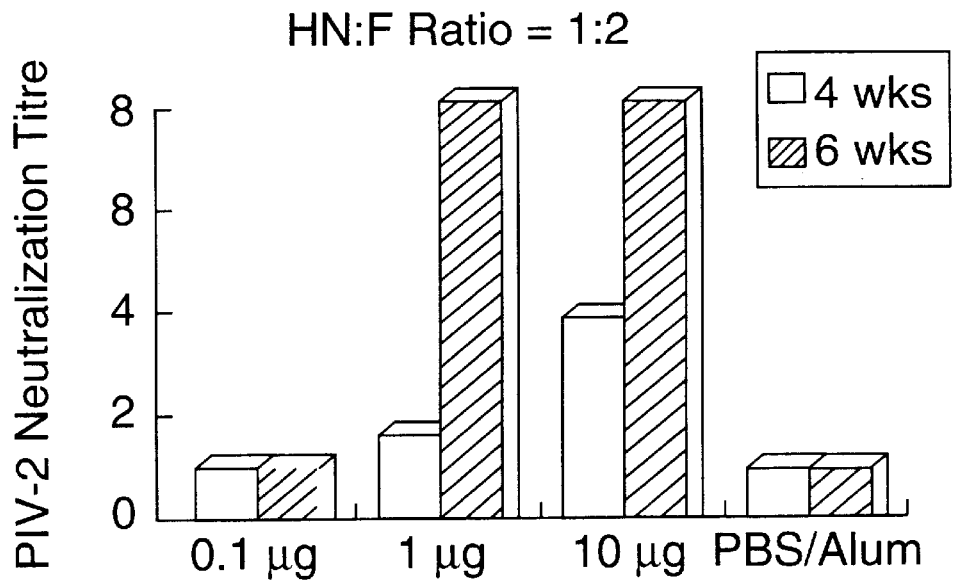
Figure 10D:
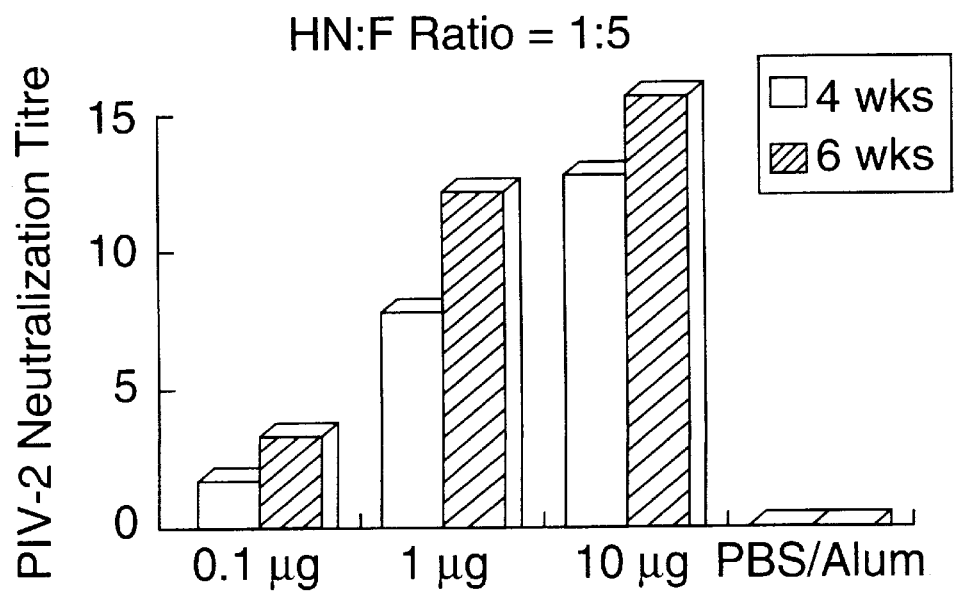
Figures 10E, 10F:
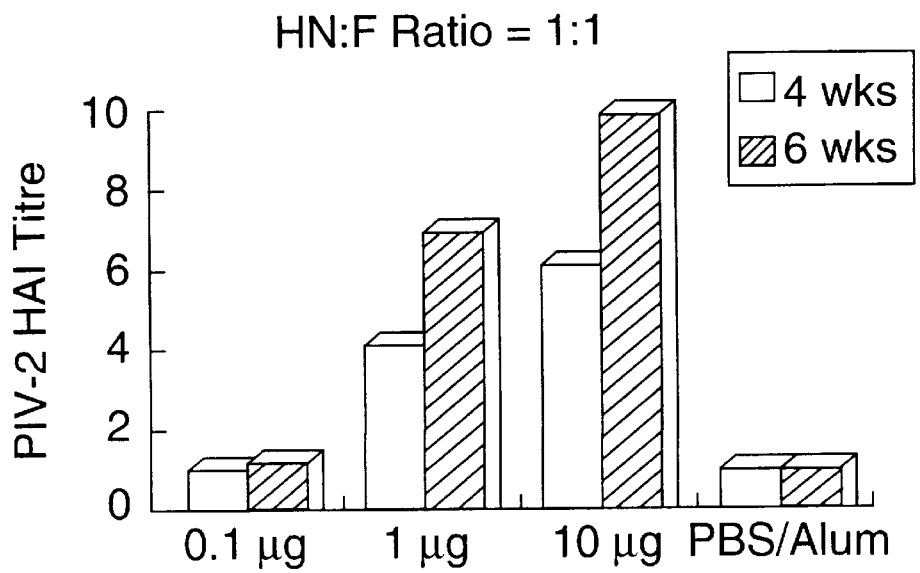
FIGS. 10(e)–10(h) show the PIV-2 hemagglutination inhibition (HAI) titres of sera from mice immunized with a mixture of separately purified parainfluenza virus type 2 HN and F glycoprotein combined in a number of ratios.
Figure 10G:
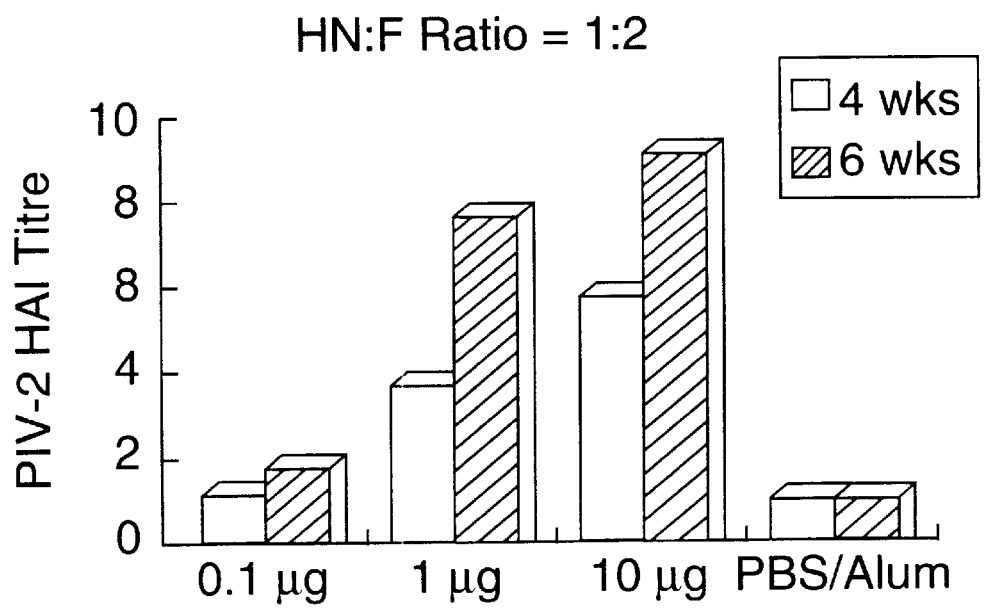
Figure 10H:
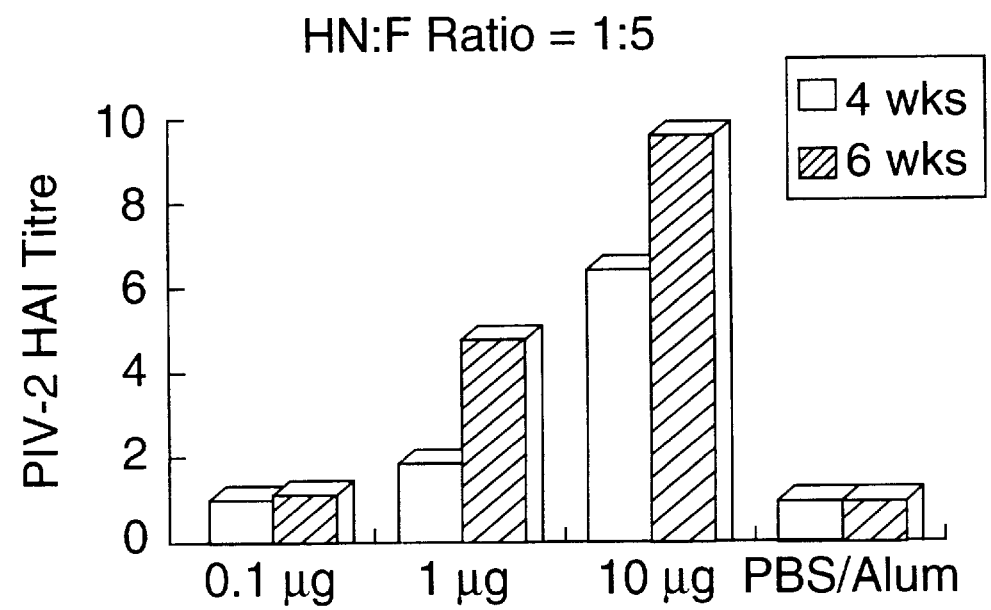

Groups of 5 mice (CD-1, 18–20 g) were immunized intraperitoneally (0.5 mL) on day 0 and day 28 with 0.1, 1, or 10 μg of PIV-2 HN&F glycoproteins adjuvanted with 3 mg/ml aluminum phosphate (alum). For each dose of glycoprotein, ratios of HN:F of 1:1, 1:2, and 1:5 were tested. Blood samples were taken on days 0, 28 and 42. Mice immunized with PBS/alum served as negative controls. Sera were analyzed for anti-HN, anti-F titres and PIV-2 specific neutralizing titres. Irrespective of the ratio of HN and F protease present in the 1 or 10 μg dose, all formulations elicited good titres of anti-HN, anti-F and PIV-2 specific neutralizing antibodies in immunized animals at 4 and 6 weeks. Results are summarized in FIGS. 8 to 10.

Example 13

Figures 11A, 11B:
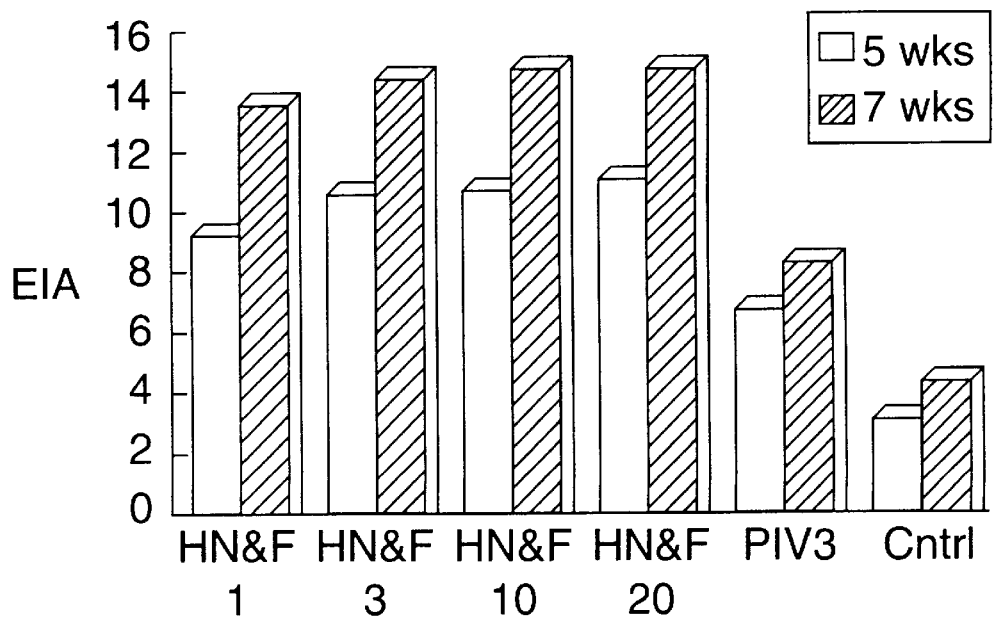
FIGS. 11(a) and 11(b) show the anti-PIV3 response in mice immunized with purified parainfluenza virus type 3 HN and F glycoprotein.
Figures 11C, 11D:
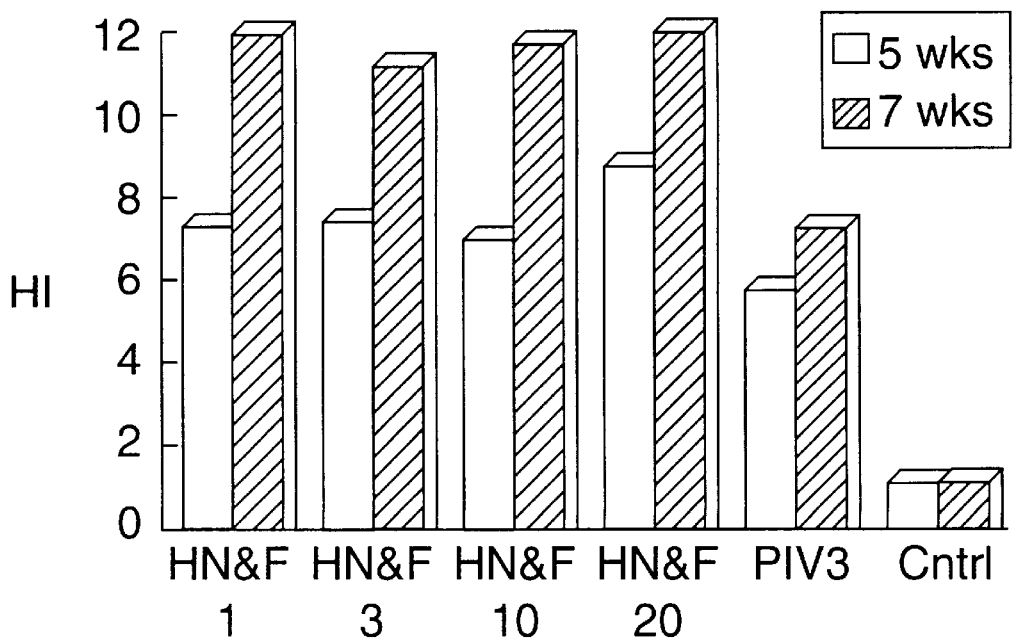
FIGS. 11(c) and 11(d) show the hemagglutination-inhibition titres of sera from mice immunized with purified parainfluenza virus type 3 HN and F glycoproteins.
Figures 11E, 11F:
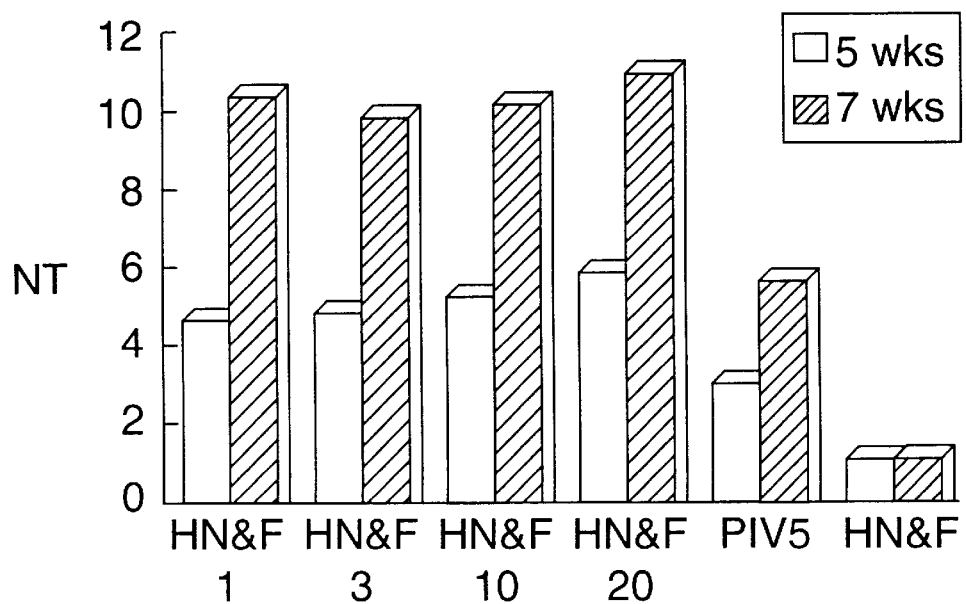
FIGS. 11(e) and 11(f) show the PIV-3 neutralization titres of sera from mice immunized with purified parainfluenza virus type 3 HN and F glycoproteins.

This Example illustrates the immunogenicity of the PIV-3 HN and F glycoproteins in mice Mice (18–20g, $CD_1$, Charles River) were immunized intraperitoneally with 0.5 ml of 1, 3, 10 and 20 μg doses of the PIV-3 HN and F glycoproteins adjuvanted with aluminum phosphate (1.5 mg per dose). For positive controls, mice were immunized intranasally with live PIV-3 ($10^5$ $TCID_{50}$) and for negative controls, mice were immunized with 1.5 mg/0.5 mL aluminum phosphate. Animals were boosted with the same dose of protein adsorbed to aluminum phosphate five weeks later. Blood samples were taken on days 0, 35 and 49. Haemagglutination inhibition (HAI), neutralizing and anti-PIV-3 ELISA titres were measured in immune sera. High titres of anti-PIV-3, HAI and neutralizing antibodies were present in the sera of animals immunized with either 1, 3, 10 or 20 μg at 5 and 7 weeks. Results are shown in FIGS. 11(a) to 11(c).

Example 14

This Example illustrates the immunogenicity of the PIV-3 HN and F glycoproteins in guinea pigs.

Figures 12A, 12B:
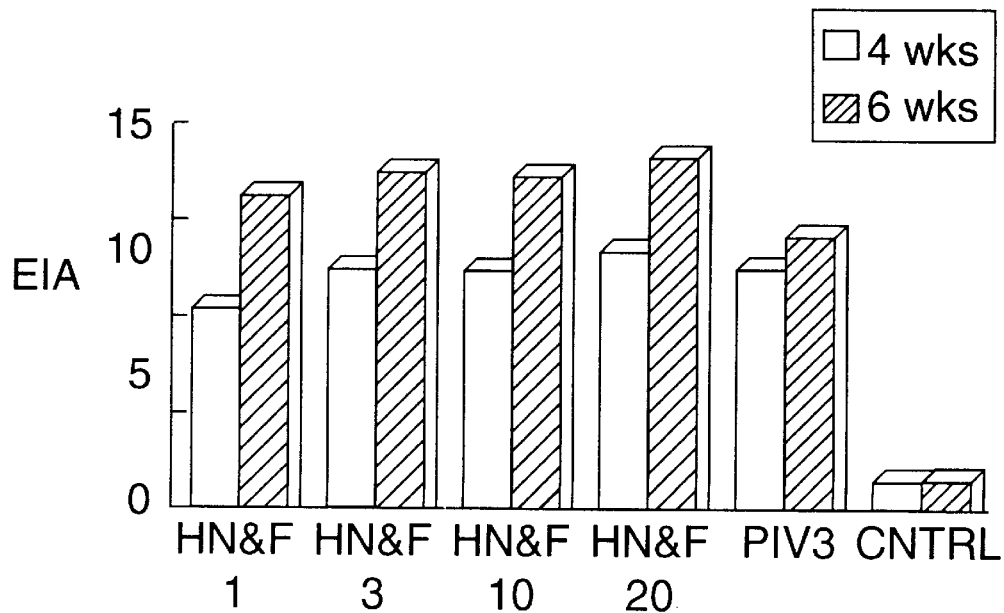
FIGS. 12(a) and 12(b) show the anti-PIV3 response in guinea pigs immunized with purified parainfluenza virus type 3 HN and F glycoproteins.
Figures 12C, 12D:
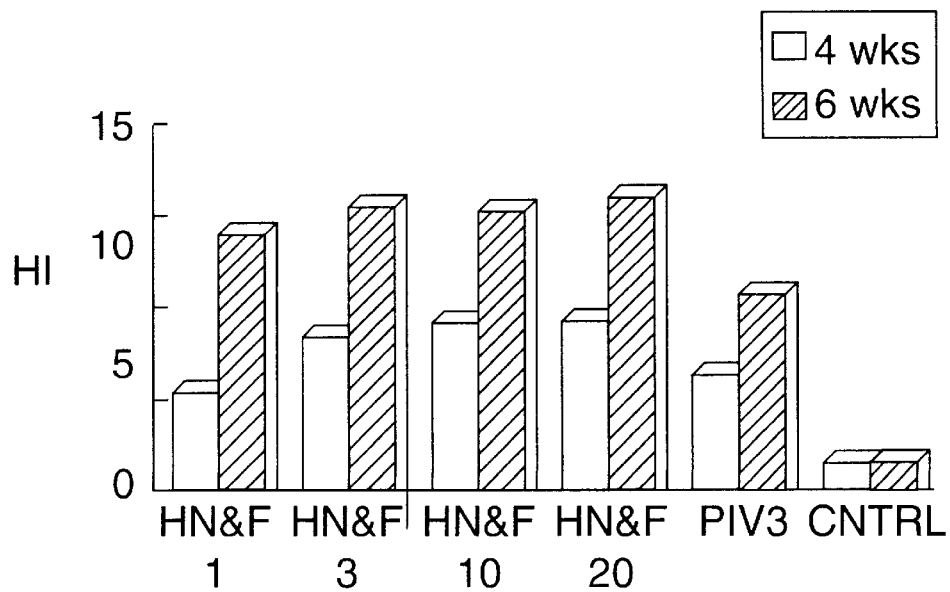
FIGS. 12(c) and 12(d) show the hemagglutination-inhibition titres of sera from guinea pigs immunized with purified, parainfluenza virus type 3 HN and F glycoproteins.
Figures 12E, 12F:
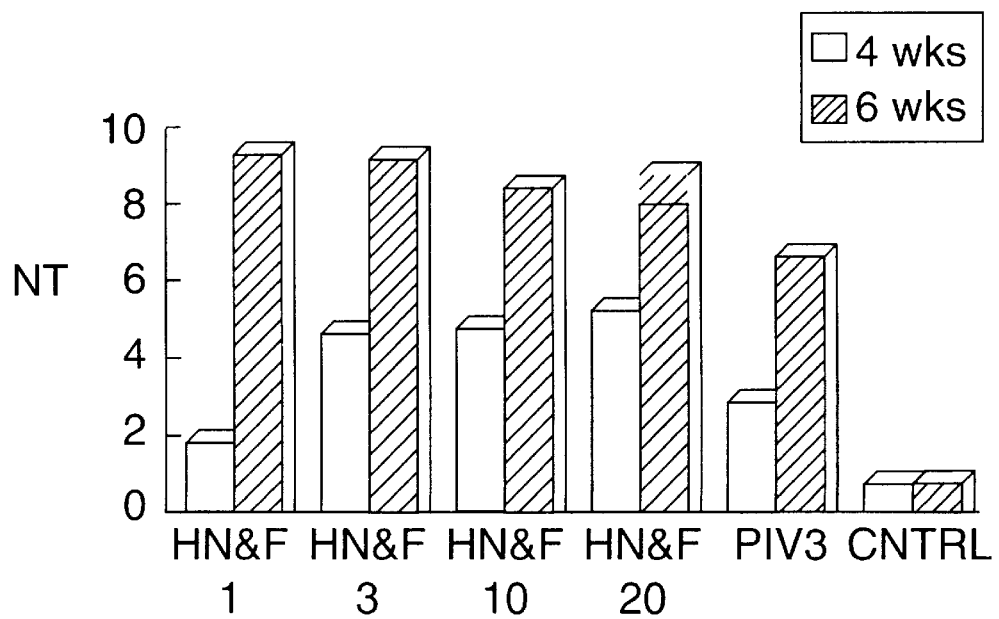
FIGS. 12(e) and 12(f) show the PIV-3 neutralization titres of sera from guinea pigs immunized with purified parainfluenza virus type 3 HN and F glycoproteins.
Figures 13A, 13B:
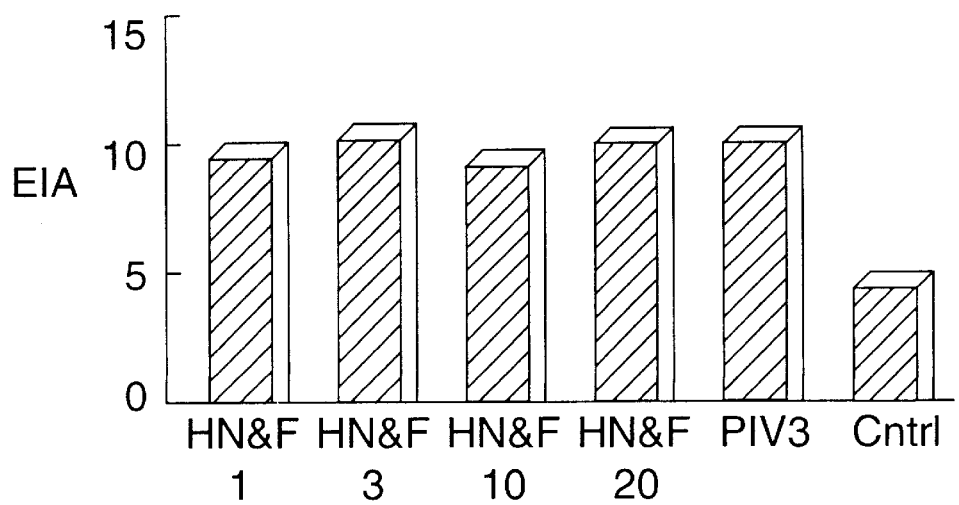
FIGS. 13(a) and 13(b) show the anti-PIV-3 antibody response in hamsters immunized with purified parainfluenza type 3 HN and F glycoproteins.
Figures 13C, 13D:
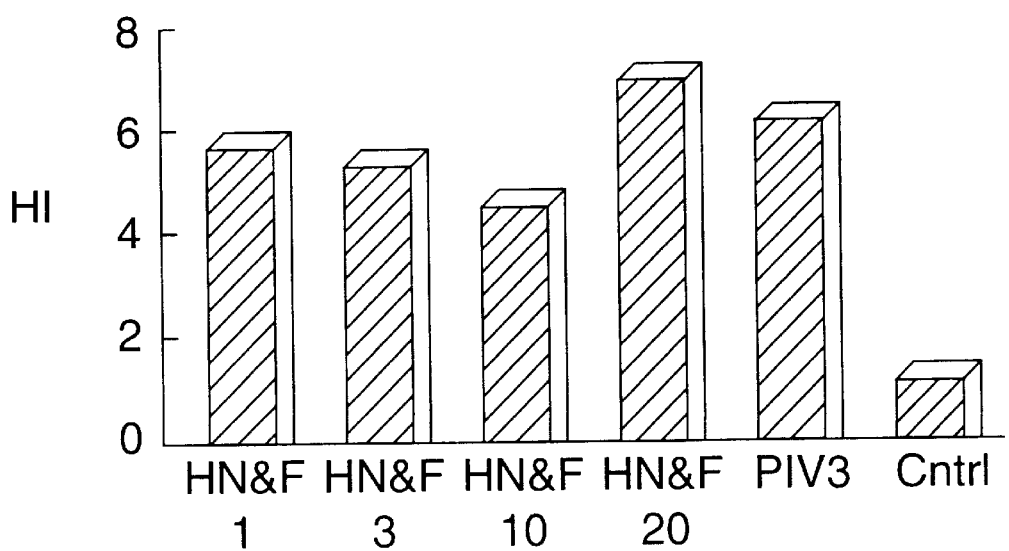
FIGS. 13(c) and 13(d) show the hemagglutination-inhibition titres of sera from hamsters immunized with purified parainfluenza type 3 HN and F glycoproteins.
Figures 13E, 13F:
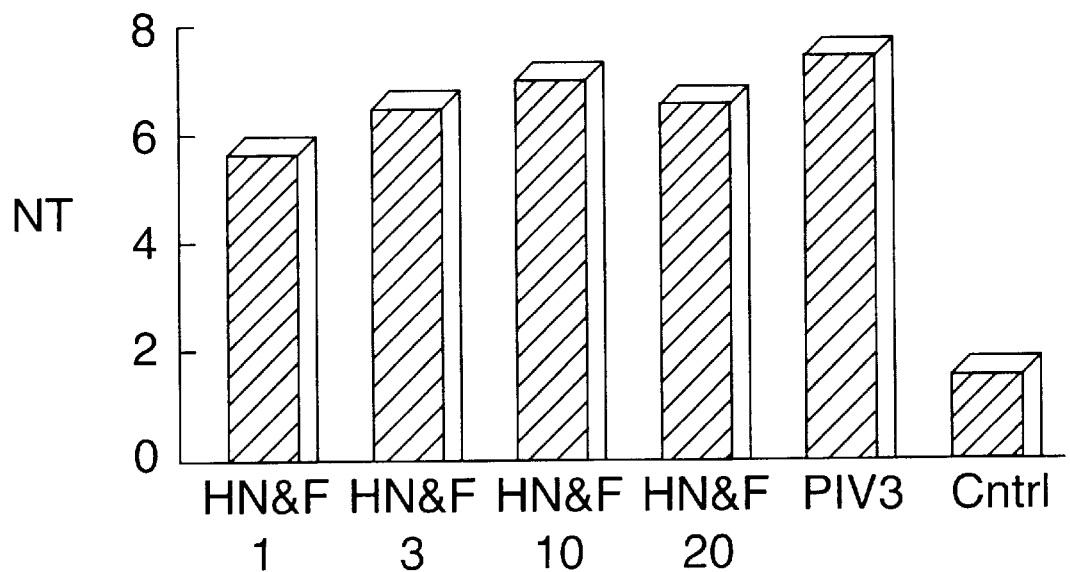
FIGS. 13(e) and 13(f) show the PIV-3 neutralization titres of sera from mice immunized with purified parainfluenza type 3 HN and F glycoproteins.
Figures 13G, 13H:
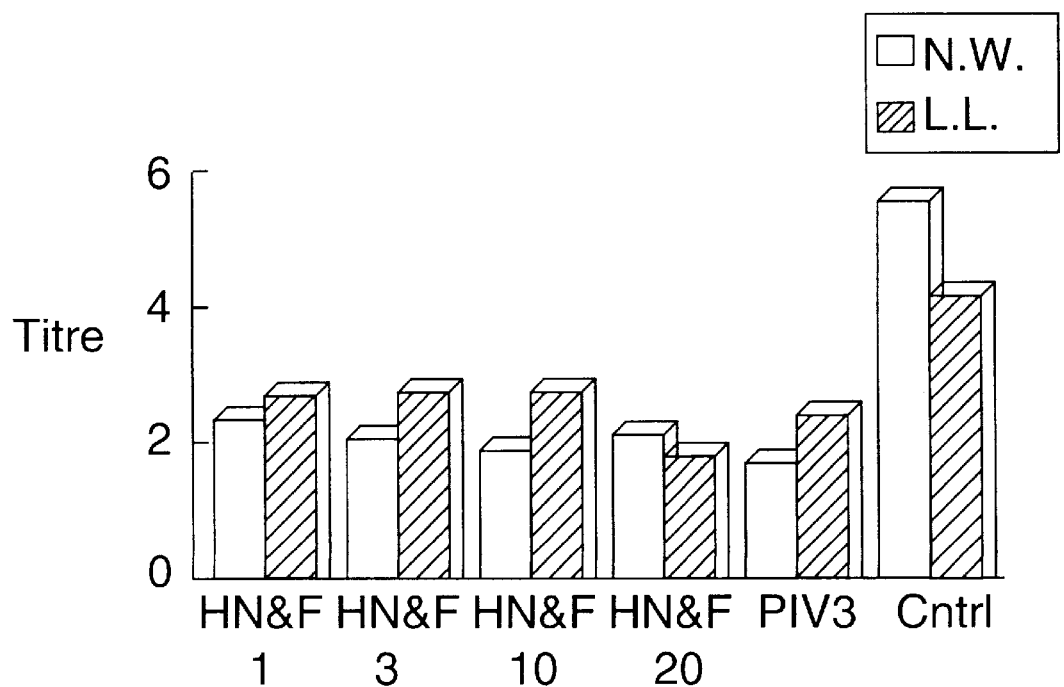
FIGS. 13(g) and 13(h) show the PIV-3 titres in nasal washes and lung lavages from hamsters immunized with purified parainfluenza type 3 HN and F glycoproteins and challenged with live PIV-3.

Guinea pigs (300 g, Buchberg) were immunized intramuscularly (0.5 ml) with 1, 3, 10 and 20 μg doses of PIV-3 HN and F glycoproteins adjuvanted with aluminum phosphate (1.5 mg). Animals immunized intranasally with $10^5$ $TCID_{50}$ of live PIV-3 served as positive controls and animals immunized with adjuvant alone (1.5 mg aluminum phosphate/0.5 ml) served as negative controls. Animals were boosted with same dose in aluminum phosphate four weeks later. Blood samples were taken at days 0, 14, 28, 42 and 56 and the HI, NT and Anti-PIV-3 ELISA titres in the sera was determined. After a booster injection there was no significant difference in these titres between any doses in any assay. These results are shown in FIGS. 12(a) to 12(c).

Example 15

This Example illustrates the ability of the PIV-3 HN and F glycoproteins to elicit a protective immune response in hamsters.

Hamsters (female, 4–6 weeks old) were immunized intramuscularly (0.5 ml) with 1, 3, 10 or 20 μg doses of the co-purified PIV-3 HN and F preparations adjuvanted with aluminum phosphate (1.5 mg). The animals were boosted with the same doses in aluminum phosphate at day 28. Animals immunized intranasally with PIV-3 ($10^5$ $TCID_{50}$) served as positive controls and animals immunized with aluminum phosphate (1.5 mg/0.5 ml) served as negative controls. Blood samples were taken at days 0, and 28. HI, NT and anti-PIV-3 ELISA titres were measured in the sera from the 4 week bleed. Good primary HAI and neutralizing response was observed for all doses. At day 42, animals were challenged intranasally with live PIV-3 ($10^5$ $TCID_{50}$/animal). Four days later, the animals were sacrificed. Virus titres were determined in bronchoalveolar lavages and nasal washes. Immunization with two 1 μg doses of the glycoproteins protected the upper and lower respiratory tracts of hamsters from subsequent infection with PIV-3. A significant reduction in virus titres in the lung lavages and nasal washes (>3 log reduction at all doses). These results are summarized in FIGS. 13(a) to 13(d).

Example 16

This Example illustrates the ability of the PIV-3 HN and F glycoprotein preparation to elicit a protective immune response in cotton rats.

Figures 14A, 14B:
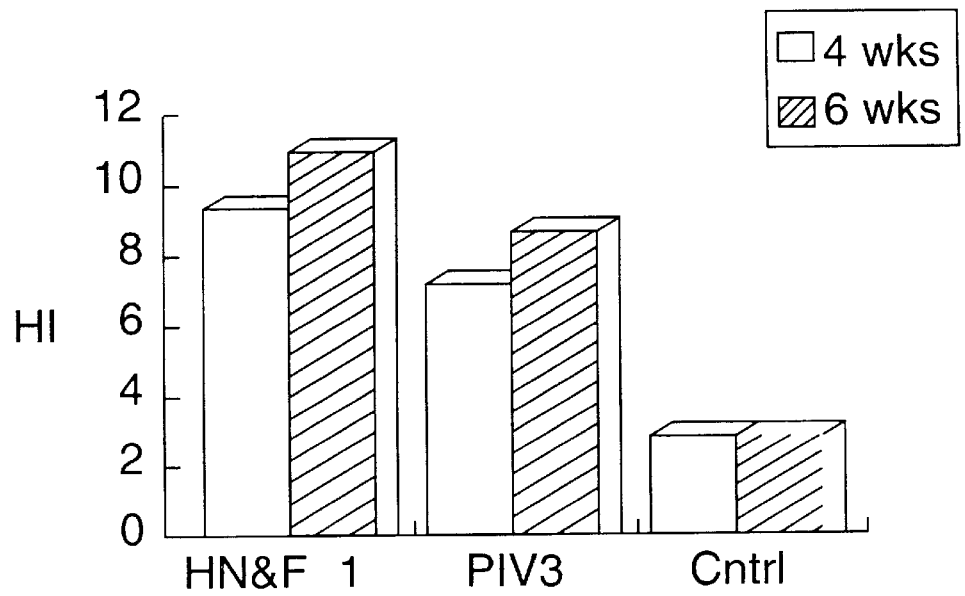
FIGS. 14(a) and 14(b) show the hemagglutination-inhibition titres of sera from cotton rats immunized with purified parainfluenza type 3 HN and F glycoproteins.
Figures 14C, 14D:
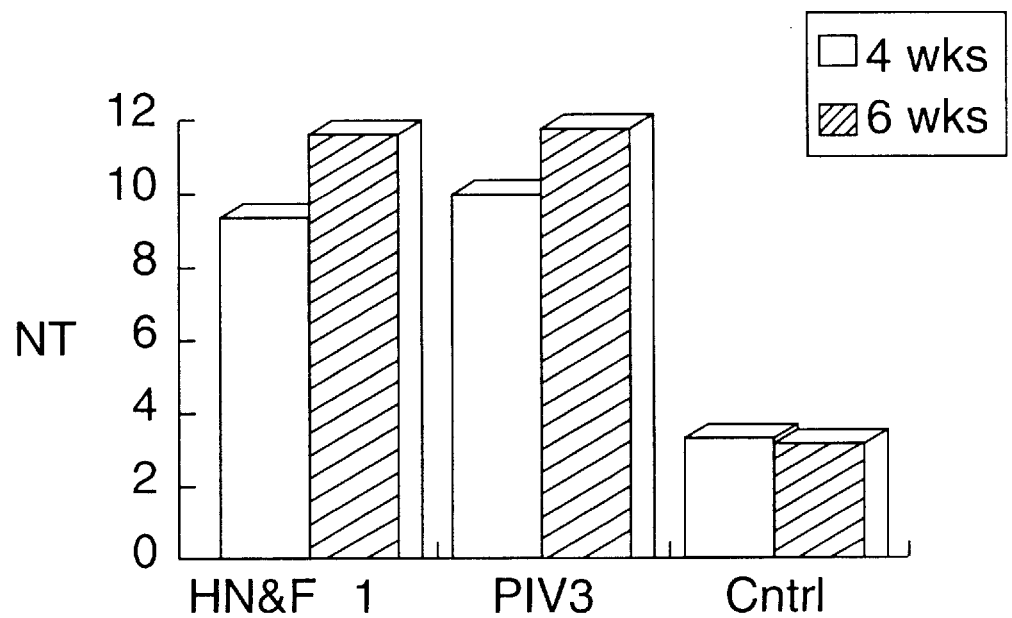
FIGS. 14(c) and 14(d) show the PIV-3 neutralization titres of sera from cotton rats immunization with purified parainfluenza type 3 HN and F glycoproteins.
Figure 14E:
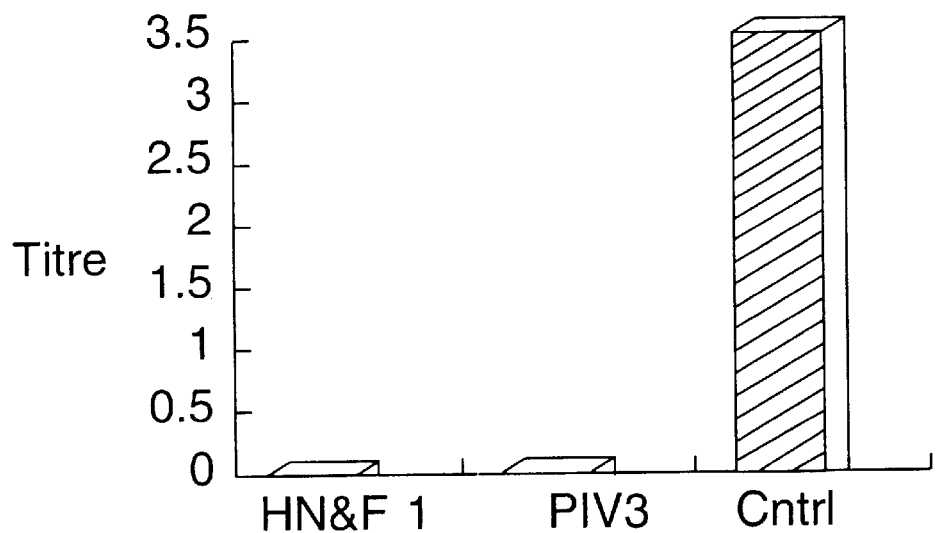
Figures 15A, 15B:
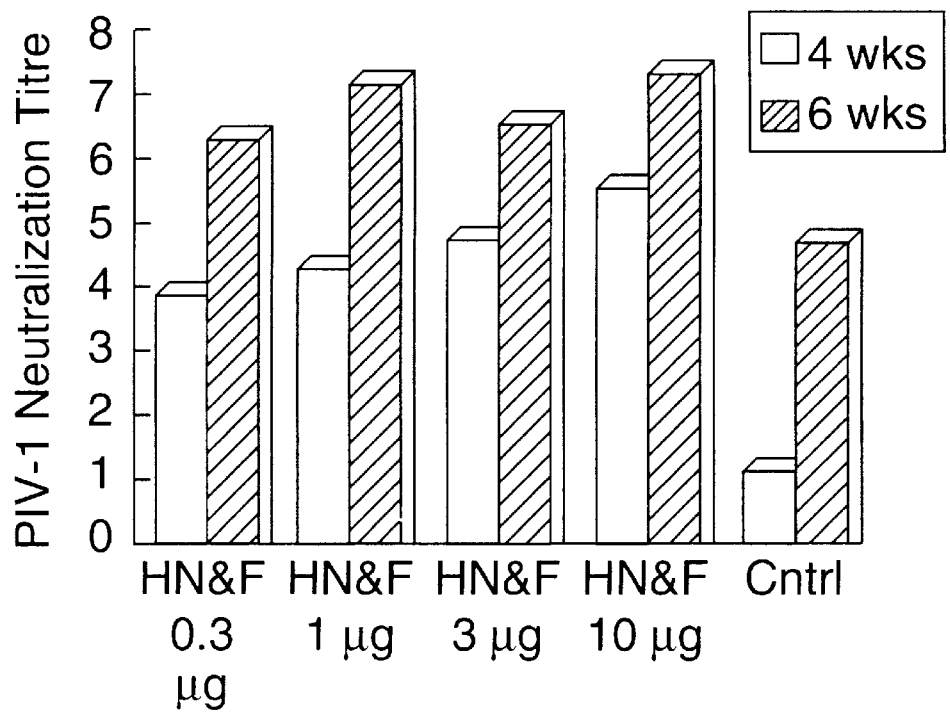
FIGS. 15(a) and 15(b) show the PIV-1 neutralization titres at sera from mice immunized with a trivalent vaccine comprising HN and F glycoproteins from parainfluenza virus types 1, 2 and 3.
Figures 15C, 15D:
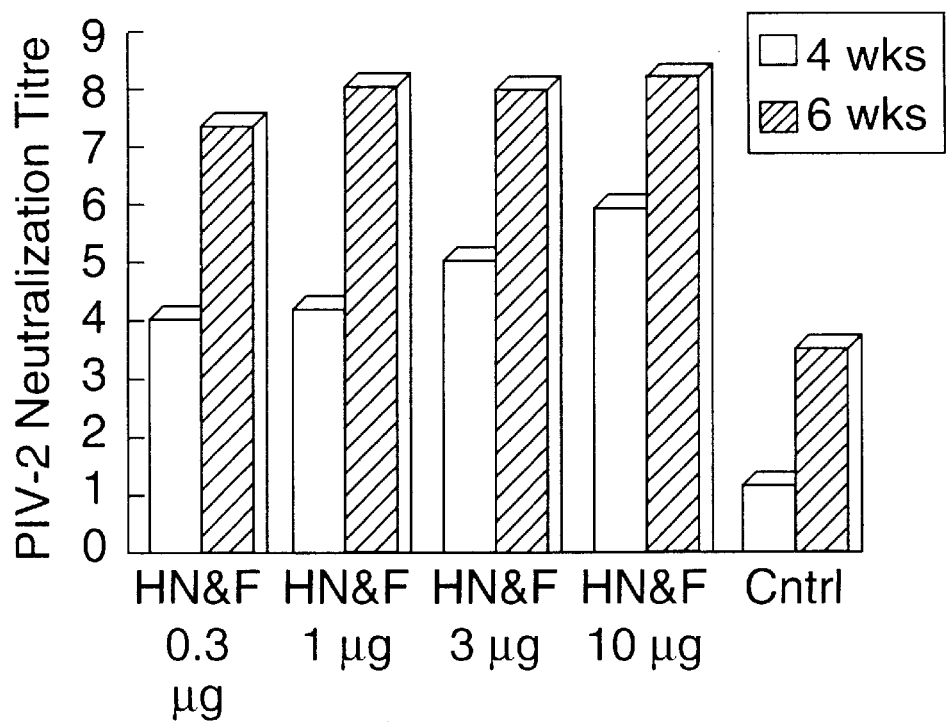
FIGS. 15(c) and 15(d) show the PIV-2 neutralization titres at sera from mice immunized with a trivalent vaccine comprising HN and F glycoproteins from parainfluenza virus types 1, 2 and 3.
Figures 15E, 15F:
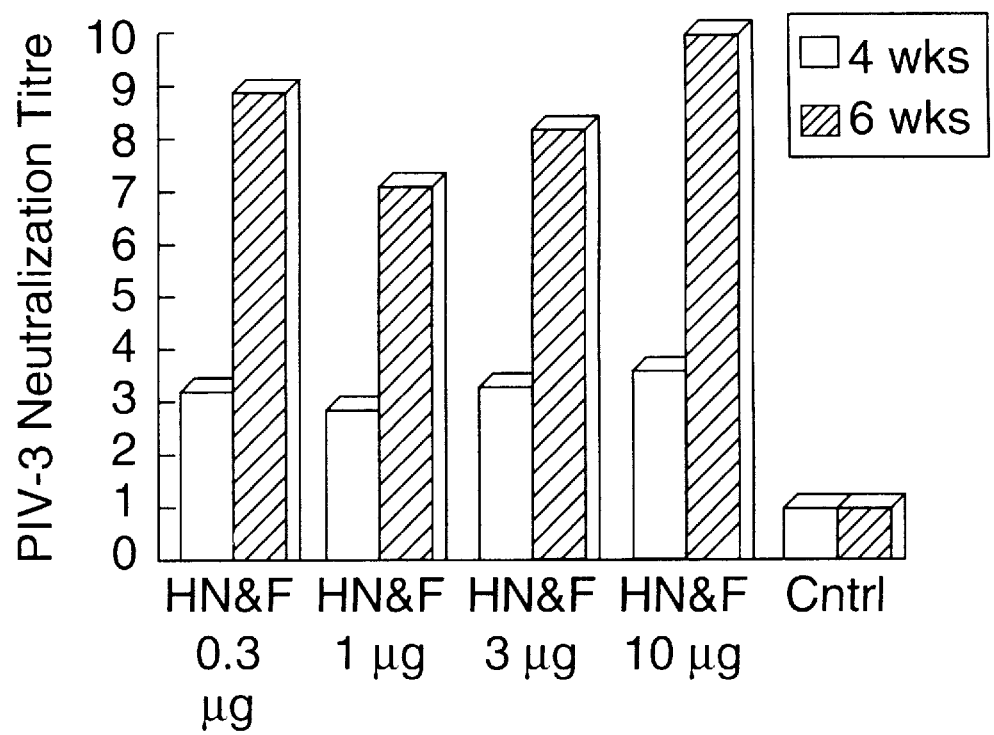
FIGS. 15(e) and 15(f) show the PIV-3 neutralization titres at sera from mice immunized with a trivalent vaccine comprising HN and F glycoproteins from parainfluenza virus types 1, 2 and 3.

Cotton rats (Sigmodon fulviventor, 4–6 weeks old) were immunized intramuscularly (0.4 ml) with a 1 μg dose of the co-purified PIV-3 HN & F glycoprotein preparation adjuvanted with aluminum phosphate (1.0 mg/dose). On day 28, the animals were bled and boosted with the same dose of antigen in aluminum phosphate. Seven days after the booster injection, animals were bled and challenged with PIV-3. Four days after the challenge, the animals were sacrificed and the lungs removed. The sera were analysed for Hemagglutination inhibition (HAI) titres and neutralization titres. A single injection of the HN and F glycoprotein preparation induced a strong neutralization and HAI response. Boosting the animals with an equivalent dose of protein enhanced the antibody responses. Titres observed were similar to those obtained following live virus immunization. No PIV-3 virus was recovered from the lungs of immunized animals. These results are summarized in FIGS. 14(*a*) to 14(*c*).

Example 17

This Example illustrates the immunogenicity of the PIV-3 HN and F glycoprotein preparation in a primate.

A young adult male Cynomologous macaque (4–5 kg) was immunized intramuscularly with 0.5 ml of sample containing 50 μg of PIV-3 HN and F and 1.5 mg aluminum phosphate and boosted six weeks later with an equivalent dose. Blood samples were taken on days 0, 28, 42, 56, 70, 84 and 112. Hematological and biochemical tests were performed. Serum was tested for PIV-3 neutralizing and HAI antibodies as well as for anti-HN and anti-F antibodies by ELISA. All hematological and biochemical analyses were within normal limits. Sera from the immunized animal had good titres of anti-HN, anti-F, RAI and neutralizing antibodies at all time points tested. The antibody responses are shown in Table 4.

Example 18

This Example illustrates the clinical testing of parainfluenza virus type 3 (PIV-3) vaccines in humans.

Two phase I human clinical studies were conducted to test the safety and immmunogenicity of a single dose of the PIV-3 subunit vaccine. Both studies were conducted after receipt of an Investigational New Drug (IND) regulatory approval from the Canadian Federal Health Protection Branch. The PIV-3 vaccine consisted of 20 μg of copurified HN and F glycoproteins adsorbed onto 1.5 mg of aluminum phosphate.

The first study involved 40 healthy adults, 20 of whom received the PIV-3 vaccine and 20 of whom received a control vaccine. The second study involved 40 healthy children aged 24 to 36 months, 23 of which received PIV-3 and 17 the control vaccine. All study subjects were followed for 7 to 8 months. The study in children included active surveillance for respiratory infections during the entire extended follow up. Both studies were double blinded.

Safety was assessed after each vaccination for local and systemic reactions. Reactions to the PIV-3 vaccine within the first 72 hours were transient and minor and the results presented in Table 5(*a*) and 5(*b*).

Serum antibody levels were determined using HN- and F-specific ELISAs, HAI and virus neutralization assays. The results are in Table 6 below and shows that recipients of the Parainfluenza 3 subunit vaccine had significantly greater post-vaccination antibody titres as measured by all tests in adults and by HAI, anti-F ELISA, anti-HN ELISA in the children. These results demonstrate that the PIV-3 HN and F glycoprotein containing vaccine is immunogenic in humans.

Example 19

This Example illustrates the immunogenicity in mice of a trivalent vaccine containing HN and F glycoproteins from PIV-1, 2, and 3.

Groups of 5 mice (CD-1, 18–20 g) were immunized intraperitoneally (0.5 mL) on day 0 and day 28 with 0.3, 1, 3, or 10 μg of a mixture of PIV-1, 2 and 3 HN&F glycoproteins (i.e. for a 10 μg dose there would be 10 μg of PIV-1 glycoproteins, 10 μg of PIV-2 glycoproteins, and 10 μg of PIV-3 glycoproteins) adjuvanted with 3 mg/ml aluminum phosphate (alum). Purified PIV-2 HN and F glycoproteins were mixed in a 1:1 ratio (eg. a 10 μg dose would contain 5 μg of HN and 5 μg of F), whereas the HN and F preparations from PIV-1 and PIV-3 were not adjusted due to their co-purification. Blood samples were taken on days 0, 28 and 42. Mice immunized with PBS/alum served as negative controls sera were analyzed for specific neutralizing titres against all three PIV types. Moderate neutralizing antibody responses against each of the three types of parainfluenza viruses were observed at 4 weeks and strong neutralizing responses were seen at 6 weeks for all doses tested. Results are summarized in FIGS. 14(*a*) to 14(*c*).

Example 20

This Example illustrates the stability of the HN and F glycoprotein preparation after adsorption to aluminum phosphate.

PIV-3 HN and F glycoproteins were stored at 6° C. and tested at 3, 6, 9, 15 and 18 months later. Stability was evaluated by SDS-PAGE and immunoblot analyses and by immunogenicity testing in mice. No change in appearance was observed at any time point. Typical SDS-PAGE, anti-HN and anti-F antibody binding were observed. No evidence of aggregation, precipitation or degradation was observed.

CD1 mice were immunized intraperitoneally with 0.5 mL of the PIV-3 HN and F glycoproteins adsorbed to aluminum phosphate. Several doses of the glycoproteins were tested at each time point. The mouse immunogenicity data are summarized are Table 6. No significant changes in immunogenicity were observed after 18 months of storage at 6° C.

TABLE 1

PIV-1 HN and F glycoprotein production in fermentor

| Sample | Volume (L) | HA units/ 50 μl | % HA recovery | Log $TCID_{50}$/ml | ELISA μg/ml HN | ELISA μg/ml F | % ELISA recovery HN | % ELISA recovery F |
|---|---|---|---|---|---|---|---|---|
| Harvest | 150 | 256 | 100 | 8.7 | 2.85 | 0.34 | | |
| Filtrate | 150 | 128 | 50 | 8.2 | 2.29 | 0.22 | 100 | 100 |
| Concentrate | 1 | 32768 | >100 | 10.3 | 260.55 | 25.24 | 76 | 76 |
| Harvest | 150 | 16 | 100 | 8.7 | 6.02 | 0.80 | | |

TABLE 1-continued

PIV-1 HN and F glycoprotein production in fermentor

| Sample | Volume (L) | HA units/ 50 µl | % HA recovery | Log TCID$_{50}$/ml | ELISA µg/ml HN | F | % ELISA recovery HN | F |
|---|---|---|---|---|---|---|---|---|
| Filtrate | 150 | 16 | 100 | 9.0 | 5.03 | 0.89 | 100 | 100 |
| Concentrate | 1 | 1024 | 43 | 11.2 | 567.74 | 64.87 | 75 | 49 |
| Harvest | 150 | 64 | 100 | 8.5 | 3.73 | 0.44 | | |
| Filtrate | 150 | 64 | 100 | 8.3 | 3.67 | 0.43 | 100 | 100 |
| Concentrate | 1 | 16384 | >100 | 10.1 | 227.18 | 33.85 | 41 | 52 |
| Harvest | 150 | 256 | 100 | 8.8 | 5.13 | 0.55 | | |
| Filtrate | 150 | 512 | >100 | 8.7 | 5.10 | 0.54 | 100 | 100 |
| Concentrate | 1 | 32768 | 43 | 10.3 | 382.4 | 40.6 | 50 | 50 |
| Harvest | 150 | 256 | 100 | 8.7 | 4.83 | 0.31 | | |
| Filtrate | 150 | 512 | >100 | 8.7 | 10.21 | 1.02 | 100 | 100 |
| Concentrate | 1 | 131072 | >100 | 10.7 | 398.21 | 28.87 | 26 | 19 |
| Harvest | 150 | 256 | 100 | 7.0 | 3.75 | 0.42 | | |
| Filtrate | 150 | 256 | 100 | 6.7 | 3.38 | 0.377 | 100 | 100 |
| Concentrate | 1 | 16384 | 43 | 9.5 | 313.8 | 45.2 | 62 | 80 |
| Harvest | 150 | 256 | 100 | 8.3 | 0.65 | 0.04 | | |
| Filtrate | 150 | 256 | 100 | 8.0 | 0.64 | 0.04 | 100 | 100 |
| Concentrate | 1 | 32768 | 85 | 10.7 | 42.3 | 2.91 | 44 | 49 |
| Harvest | 150 | 256 | 100 | 9.0 | 5.47 | 0.42 | | |
| Filtrate | 150 | 128 | 50 | 9.0 | 4.54 | 0.42 | 100 | 100 |
| Concentrate | 1 | 16384 | 85 | 11.0 | 479.917 | 55.2 | 70 | 88 |

TABLE 2

PIV-2 HN and F glycoprotein production in fermentor

| Sample | Volume (L) | HA units/50 µl | % HA recovery | Log TCID$_{50}$/ml | ELISA µg/ml Whole virus | F |
|---|---|---|---|---|---|---|
| Harvest | 120 | 16 | 100 | 8.2 | | |
| Filtrate | 120 | 16 | 100 | 7.7 | | |
| Concentrate | 2.15 | 1024 | >100 | 8.8 | 6488 | |
| Harvest | 120 | 16 | 100 | 8.3 | | |
| Filtrate | 120 | 16 | 100 | 8.2 | | |
| Concentrate | 2.05 | 2048 | >100 | 9.5 | 2263 | |
|

TABLE 3

Summary of PIV-3 Fermentor Data

| Sample | Volume (L) | HA units/50 $\mu$l | % HA recovery | Log $TCID_{50}$/ml | ELISA $\mu$g/ml | % ELISA recovery |
|---|---|---|---|---|---|---|
| Harvest | 90 | 256 | 100 | 8.8 | — | — |
| Filtrate | 140 | 256 | 155 | 8.7 | 17.9 | 100 |
| Concentrate | 2.6 | 262144 | >100 | 10.5 | 881.1 | 91.4 |
| Harvest | 95 | 512 | 100 | 8.7 | — | — |
| Filtrate | 100 | 512 | 105 | 7.8 | 15.5 | 100 |
| Concentrate | 2.0 | 262144 | >100 | 10.0 | 956.2 | 123 |
| Harvest | 90 | 256 | 100 | 8.3 | — | — |
| Filtrate | 90 | 128 | 50 | 7.5 | 8.6 | 100 |
| Concentrate | 2.3 | 16384 | >100 | 9.8 | 446.3 | 133 |
| Harvest | 100 | 512 | 100 | 9.7 | — | — |
| Filtrate | 100 | 512 | 100 | 9.7 | 30.5 | 100 |
| Concentrate | 2.8 | 16384 | 89.6 | 10.5 | 1181.2 | 109 |
| Harvest | 100 | 256 | 100 | 8.5 | — | — |
| Filtrate | 100 | 128 | 50 | 8.5 | 15.7 | 100 |
| Concentrate | 2.4 | 8192 | 76.8 | 10.3 | 496.6 | 76 |
| Harvest | 110 | 128 | 100 | 8.7 | — | — |
| Filtrate | 110 | 64 | 50 | 8.2 | 12.8 | 100 |
| Concentrate | 2.6 | 4096 | 75.6 | 10.0 | 521.1 | 98.6 |

TABLE 4

Immunogenicity of PIV-3 HN & F Glycoproteins in a Macaque

| Day | Neutralization Titre | Hemagglutination Inhibition Titre | Anti-HN ELISA Titre | Anti-F ELISA Titre |
|---|---|---|---|---|
| 0 | <10 | 40 | 350 | 260 |
| 28 | 5120 | 5120 | 31000 | 25500 |
| 42 | 2560 | 2560 | 21200 | 11300 |
| 56 | 640 | 1280 | 15600 | 12000 |
| 70 | 320 | 1280 | 18500 | 14300 |
| 84 | 320 | 320 | 12500 | 10000 |
| 112 | 320 | 320 | 10000 | 7800 |

TABLE 5(a)

Adult reactions at 24 and 72 hours

| Reactions | 24 Hour PIV-3 (n = 20) | 72 Hour PIV-3 (n = 19)+ |
|---|---|---|
| Local | | |
| Redness | 5% | 0 |
| Swelling | 0 | 0 |
| Discomfort | 85%* | 16% |
| Systemic | | |
| Feverishness | 0 | 5% |
| Sore Throat | 0 | 11% |
| Congestion | 10% | 16% |
| Cough | 0 | 5% |
| Headache | 20% | 16% |
| Tireness | 15% | 32% |
| Nausea | 5% | 0 |
| Vomiting | 0 | 0 |
| Achiness/Malaise | 5% | 5% |
| Itchiness | 0 | 5% |
| Medical Consultation | 0 | 0 |
| Other Problems | 0 | 0 |

TABLE 5(b)

Child reactions at 24 and 72 hours to PIC-3 vaccines

| Reactions | 24 Hour PIV-3 (n = 20) | 72 Hour PIV-3 (n = 19)+ |
|---|---|---|
| Local | | |
| Redness | 0 | 0 |
| Swelling | 0 | 0 |
| Discomfort | 9%* | 4% |
| Systemic | | |
| Congestion | 0 | 9% |
| Cough | 0 | 9% |
| Sore Throat | 0 | 4% |
| Rash | 0 | 0 |
| Fussiness | 17% | 13% |
| Crying | 13% | 13% |
| Less Active | 9% | 9% |
| Vomiting | 0 | 4% |
| Diarrhea | 4% | 9% |
| Shaking Episode | 0 | 0 |
| Medical Consultation | 0 | 0 |
| Other Problems | 0 | 0 |

+Data for one subject was collected outside the 72 hours window
*p = 0.08, Chi-Square (Yates corrected)
n = number of vaccinated subjects

TABLE 6

Immunogenicity of PIV-3 vaccine in humans

Geometric Mean Titres

|  | anti-HN | | anti-F | | HAI | | NA | |
| --- | --- | --- | --- | --- | --- | --- | --- | --- |
|  | Pre | Post | Pre | Post | Pre | Post | Pre | Post |
| Adults | 2.56 | 7.25 | 3.0 | 12.05 | 152.02 | 1420.25 | 123.41 | 415.88 |
| Children | 0.97 | 5.69 | 0.90 | 3.12 | 53.83 | 398.98 | 11.84 | 59.71 |

TABLE 7

Stability of PIV-3 IIN and F Glycoproteins Adsorbed to Aluminum Phosphate

| Time of Storage (months) | Dose ($\mu$g) | III Titre $\log_2(III/5) \pm SE$ | NT Titre $\log_2(NT/5) \pm SE$ | Anti-PIV-3 ELISA Titre $\log_2(EIA/100) \pm SE$ |
| --- | --- | --- | --- | --- |
| 0* | 0.3 | 6.0 ± 1.1 | 2.3 ± 1.2 | 7.8 ± 1.8 |
|  | 1.0 | 8.9 ± 1.2 | 3.6 ± 1.2 | 9.6 ± 1.3 |
|  | 3.0 | 8.3 ± 0.9 | 4.2 ± 1.2 | 10.2 ± 1.3 |
|  | 10.0 | 9.0 ± 0.6 | 5.1 ± 0.7 | 10.8 ± 1.1 |
| 3* | 1.0 | 7.2 ± 0.4 | 4.8 ± 0.7 | 9.4 ± 0.8 |
|  | 3.0 | 7.4 ± 1.4 | 5.0 ± 0.9 | 11.0 ± 1.3 |
|  | 10.0 | 7.0 ± 0.6 | 5.4 ± 0.8 | 11.0 ± 0.0 |
|  | 20.0 | 8.6 ± 0.8 | 6.0 ± 0.0 | 11.4 ± 0.8 |
| 6 | 0.3 | 6.2 ± 1.2 | 3.2 ± 1.0 | 10.2 ± 0.8 |
|  | 1.0 | 6.6 ± 0.5 | 4.0 ± 1.0 | 10.6 ± 0.8 |
|  | 3.0 | 7.1 ± 0.5 | 4.5 ± 0.9 | 11.0 ± 0.9 |
|  | 10.0 | 7.1 ± 1.4 | 4.9 ± 0.9 | 11.4 ± 0.8 |
| 9 | 0.3 | 7.6 ± 1.3 | 3.1 ± 0.9 | 9.7 ± 0.9 |
|  | 1.0 | 7.9 ± 0.9 | 3.8 ± 1.0 | 10.0 ± 1.0 |
|  | 3.0 | 8.6 ± 1.9 | 4.6 ± 1.4 | 10.8 ± 1.1 |
| 15 | 0.3 | 7.7 ± 1.4 | 4.0 ± 2.3 | nd |
|  | 1.0 | 8.9 ± 0.7 | 5.7 ± 1.3 | nd |
|  | 3.0 | 6.9 ± 3.7 | 6.1 ± 1.1 | nd |
| 18 | 0.3 | nd | 3.5 ± 1.4 | 8.6 ± 3.2 |
|  | 1.0 | nd | 4.0 ± 1.5 | 9.8 ± 3.2 |
|  | 3.0 | nd | 5.9 ± 0.7 | 12.0 ± 1.0 |

SE = Standard Error
nd = not determined
*Animals were bled 5 weeks after injection.

References

1. Katz, S. L. New vaccine development Establishing Priorities. Vol. 1. Washington: National Academic Press. (1985) pp. 385–396.
2. Fulginiti, V. A., Eller, J. J., Sieber, O. F., Joyner, J. W., Minamitani, M. and Meiklejohn, G. (1969) Am. J. Epidemiol. 89 (4), 435–448.
3. Chin, J., Magoffin, R. L., Shearer, L. A., Schieble, J. H. and Lennette, E. H. (1969) Am. J. Epidemiol. 89 (4), 449–463.
4. Jensen, K. E., Peeler, B. E. and Dulworth, W. G. (1962) J. Immunol. 89, 216–226.
5. Murphy, B. R., Prince, G. A., Collins, P. L., Van Wyke Coelingh, K., Olmsted, R. A., Spriggs, M. K., Parrott, R. H., Kim, H. Y., Brandt, C. D. and Chanock, R. M. (1988) Vir. Res. 11, 1–15.
6. Hall, S. L., Sarris, C. M., Tierney, E. L., London, W. T., and Murphy, B. R. (1993) J. Infect. Dis. 167, 958–962.
7. Belshe, R. B., Karron, R. A., Newman, F. K., Anderson, E. L., Nugent, S. L., Steinhoff, M., Clements, M. L., Wilson, M. H., Hall, S. L., Tierney, E. L. and Murphy, B. R. (1992) J. Clin. Microbiol. 30 (8), 2064–2070.
8. Hall, S. L., Stokes, A., Tierney, E. L., London, W. T., Belshe, R. B., Newman, F. C. and Murphy, B. R. (1992) Vir. Res. 22, 173–184.
9. Van Wyke Coelingh, K. L., Winter, C. C., Tierney, E. L., London, W. T. and Murphy, B. R. (1988) J. Infect. Dis. 157 (4), 655–662.
10. Ray, R., Novak, M., Duncan, J. D., Matsuoka, Y. and Compans, R. W. (1993) J. Infect. Dis. 167, 752–755.
11. Ray, R., Brown, V. E. and Compans, R. W. (1985) J. Infect. Dis. 152 (6), 1219–1230.
12. Ray, R. and Compans, R. W. (1987) J. Gen. Virol. 68, 409–418.
13. Ray, R., Glaze, B. J., Moldoveanu, Z. and Compans, R. W. (1988) J. Infect. Dis. 157 (4), 648–654.
14. Ray, R., Matsuoka, Y., Burnett, T. L., Glaze, B. J. and Compans, R. W. (1990) J. Infect. Dis. 162, 746–749.
15. Ray, R., Glaze, B. J. and Compans, R. W. (1988) J. Virol. 62 (3), 783–797.
16. Ewasyshyn, M., Caplan, B., Bonneau A. M., Scollard, N., Graham, S., Usman, S. and Klein, M. (1992) Vaccine 10 (6), 412–420.
17. Ambrose, M. W., Wyde, P. R., Ewasyshyn, M., Bonneau, A. M., Caplan, B., Meyer, H. L. and Klein, M. (1991) Vaccine 9, 505–511.
18. Kasel, J. A., Frank, A. L., Keitel, W. H., Taber, L. H., Glezen W. P. J. Virol. 1984; 52:828–32.
19. Lehman, D. J., Roof, L. L., Brideau, R. J., Aeed, P. A., Thomsen, D. R., Elmhammer, A. P., Wathen, M. W. and Homa, F. L. (1993) J. Gen. Virol. 74, 459–469.

20. Brideau, R. J., Oien, N. L., Lehman, D. J., Homa, F. L. and Wathen, M. W. (1993) *J. Gen. Virol.* 74, 471–477.
21. Ebata, S. N., Prevec, L., Graham, F. L. and Dimock, K. (1992) *Vir. Res.* 24, 21–33.
22. Hall, S. L., Murphy, B. R. and Van Wyke Coelingh, K. L. (1991) *Vaccine* 9, 659–667.
23. Homa, F. L., Brideau, R. J., Lehman , D. J., Thomsen, D. R., Olmsted, R. A. and Wathen, M. W. (1993) *J. Gen. Virol.* 74, 1995–1999.

Patent Applications:
Ewasyshyn, M. E., Caplan, B. I., Bonneau A. M. and Klein, M. H. WO 91/00104
Gheysen, D., Bolien, A., Blaise, L. PCT/EP92/02174 Priority Date: Sep. 23, 1991 Filing Date: Sep. 18, 1992
Compans, R. W. and Ray, R. PCT/U.S. application Ser. No. 89/03740 Filing Date: Aug. 29, 1989 Priority Date: Sep. 2, 1988
Compans, R. W. and Ray, R. PCT/U.S. application Ser. No. 88/101502 Filing Date: May 4, 1988 Priority Date: May 5, 1987
Compans, R. W. and Ray, R. U.S. Patent NO.: 4,790,987 Date of Patent: Dec. 13, 1988 Filed: Nov. 15, 1985

What we claim is:

1. A method of producing a coisolated and copurified mixture of glycoproteins of parainfluenza virus type 1 (PIV-1), which comprises:
   growing PIV-1 in a cell culture;
   separating the grown virus from the cell culture;
   solubilizing the hemagglutinin-neuraminidase (HN) and the fusion (F) envelope glycoproteins from the separated virus; and
   coisolating and copurifying the solubilized envelope glycoproteins by:
      collecting HN and F glycoprotein-containing flow-through from ion exchange chromatograghy of the solubilized envelope glycoproteins,
      loading the flow through onto a hydroxyapatite matrix, and
      selectively coeluting the HN and F glycoproteins from the hydroxyapatite matrix.

2. The method of claim 1 wherein the selectively coeluted HN and F glycoproteins are purified by tangential flow ultrafiltration.

3. The method of claim 1 wherein said coisolation and copurification further comprises selectively coprecipitating the HN and F glycoproteins from the coeluted HN and F glycoproteins, separating the coprecipitated HN and F glycoproteins from supernatant formed in said coprecipitation, and resolubilizing the separated HN and F glycoproteins.

4. A method of producing an isolated and purified individual glycoprotein of parainfluenza virus type 2 (PIV-2), which comprises:
   growing PIV-2 in a cell culture;
   separating the grown virus from the cell culture;
   solubilizing the hemagglutinin-neuraminidase (HN) and the fusion (F) envelope glycoproteins from the separated virus; and
   separately isolating and purifying the solubilized envelope glycoproteins by:
      collecting F glycoprotein-containing flow-through from ion-exchange chromatography of the solubilized envelope glycoproteins while HN glycoprotein is retained on the ion-exchange medium,
      applying the collected flow through to a hydroxyapatite matrix and collecting an F glycoprotein-containing flow through,
      selectively removing detergent used in the solubilization step from the hydroxyapatite matrix flow through to provide isolated and purified F glycoprotein; and
      eluting HN glycoprotein from the ion-exchange medium to provide isolated and purified HN glycoprotein.

5. The method of claim 4 wherein said isolated and purified HN glycoprotein is applied to a gel filtration medium to separate the HN glycoprotein from contaminants of other molecular weights.

6. The method of claim 4 wherein said isolated and purified HN glycoprotein is applied to a hydroxyapatite matrix to bind HN glycoprotein to the matrix and the HN glycoprotein is subsequently eluted therefrom.

7. The method of claim 4 wherein the isolated and purified F and HN glycoproteins are separately purified by tangential flow ultrafiltration.

8. A method of producing coisolated and copurified glycoproteins of parainfluenza virus type 3 (PIV-3), which comprises:
   growing PIV-3 in a cell culture,
   separating the grown virus from the cell culture,
   solubilizing the hemagglutinin-neuraminidase (HN) and the fusion (F) envelope glycoproteins from the separated virus, and
   coisolating and copurifying the solubilized glycoproteins free from lectin by:
      loading HN and F glycoproteins on a first ion-exchange medium while permitting contaminants to pass through the medium,
      coeluting the HN and F glycoproteins from the first ion-exchange medium,
      loading the coeluted HN and F glycoproteins onto a second ion-exchange medium in a solution at an ionic strength to effect binding of the coeluted HN and F glycoproteins and to allow contaminants to flow through the second ion exchange medium, and
      eluting the HN and F glycoprotein mixture from the second ion-exchange medium.

9. The method of claim 8 wherein the collected flow through is purified by tangential flow ultrafiltration.

* * * * *